(12) United States Patent
Hovinen

(10) Patent No.: US 7,282,581 B2
(45) Date of Patent: Oct. 16, 2007

(54) OLIGONUCLEOTIDE LABELING REACTANTS BASED ON ACYCLONUCLEOSIDES AND CONJUGATES DERIVED THEREOF

(75) Inventor: Jari Hovinen, Raisio (FI)

(73) Assignee: Wallac Oy, Turku (FI)

( * ) Notice: Subject to any disclaimer, the term of this patent is extended or adjusted under 35 U.S.C. 154(b) by 1658 days.

(21) Appl. No.: 09/985,454

(22) Filed: Nov. 2, 2001

(65) Prior Publication Data

US 2003/0118999 A1 Jun. 26, 2003

(51) Int. Cl.
*C07H 21/00* (2006.01)
*C07H 19/00* (2006.01)
(52) U.S. Cl. ............. 536/25.32; 536/25.3; 536/26.1; 536/26.8; 536/27.1; 536/27.13; 536/28.1; 536/28.6
(58) Field of Classification Search .......... 536/25.3, 536/25.32, 26.8, 27.1, 27.13, 28.1, 28.6, 536/26.1
See application file for complete search history.

(56) References Cited

OTHER PUBLICATIONS

Hovinen et al. Organic Letters, 2001, vol. 3, pp. 2473-2476.*
Augustyns et al., Nucleic Acid Research, 1991, vol. 19, pp. 2587-2593.*
Wojczewski et al., "Flourescent Oligonucleotides—Verstile Tools As Probes and Primers for DNA and RNA Analysis," *Synlett* 1667 (1999).
Beaucage et al., "The Synthesis of Modified Oligonucleotides by the Phosphoramidite Approach and Their Applications," 49 *Tetrahedron* 6123 (1993).

* cited by examiner

*Primary Examiner*—Patrick Lewis
(74) *Attorney, Agent, or Firm*—James C. Lydon

(57) ABSTRACT

The invention relates to a labeling reactant of formula (I) useful for labeling an oligonucleotide $$\begin{array}{c} G \\ | \\ E''' \\ | \\ Z' \\ | \\ E' \\ | \\ R\text{---}E\text{---}Z\text{---}E''\text{---}A \end{array} \quad (I)$$

wherein: R is a temporary protecting group. A is either a phosphorylating moiety or a solid support tethered to Z via a linker arm E". Z is a bridge point and is formed from E is a linker arm between R and Z. E' is a linker arm between Z and Z'. E" is a linker arm between Z and A. E''' is a linker arm between Z' and G. Z' is a purine or pyrimidine base. G is a protected bivalent aromatic structure, tethered to two iminodiacetic acid ester groups $N(CH_2COOR'')_2$, or G is a structure selected from the group consisting of or G is a protected functional group, or G is a protected or unprotected organic dye, hapten or a spin label.

28 Claims, 1 Drawing Sheet

SEQUENCE LISTING
<160> NUMBER OF SEQ ID NOS: 1
<210> SEQ ID NO 1
<211> LENGTH: 16
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1
gttcttcttg gagtaa                                                        16
```

OLIGONUCLEOTIDE LABELING REACTANTS BASED ON ACYCLONUCLEOSIDES AND CONJUGATES DERIVED THEREOF

FIELD OF THE INVENTION

This invention relates to compounds for labeling of oligonucleotides using either machine assisted solid phase chemistry or polymerases, and conjugates derived thereof.

BACKGROUND OF THE INVENTION

The publications and other materials used herein to illuminate the background of the invention, and in particular, cases to provide additional details respecting the practice, are incorporated by reference.

Synthetic oligonucleotides tethered to various ligands have been used as research tools in molecular biology [for reviews, see e.g. Iyer, R. P., Roland, A., Zhou, W., and Ghosh, K. *Curr. Opin. Mol. Ther.*, 1999, 1, 344; Uhlman, E. and Peyman. A. *Chem Rev*, 1990, 90, 543; English. U. and Gauss, D. H. *Angew. Chem. Int. Ed. Engl.* 1991, 30, 613. Beaugace and Iyer, *Tetrahedron*, 1993, 49, 6123.; Wojczewski, C., Stolze, K. and Engels, J. W. *Synlett*, 1999, 1667]. They have been applied to genetic analysis, and to elucidate mechanism of gene function. Oligonucleotides carrying reporter groups have had widespread use for automated DNA sequencing, hybridization affinity chromatography and fluorescence microscopy, Oligonucleotide-biotin conjugates axe widely used as hybridization probes. Antisense oligonucleotides covalently linked to intercalators, chain cleaving or alkylating agents have been shown to be efficient as gene expression regulators. The sequence specific artificial nucleases, when targeted against mRNA, may find applications even as chemotherapeutics.

The labels can be attached to the target oligonucleotides or polynucleotides either chemically or enzymatically. The chemical approach includes often preparation of modified building blocks, and their subsequent insertion into synthetic oligonucletides during oligonucleotide synthesis. Alternatively, natural DNA can be transformed, for example by bisulfite catalyzed transamination of cytosine residues [*Biochemistry*, 1980, 19, 1774] followed by labeling of the amino functions with appropriate label molecules, The enzymatic approach, in turn, consists of preparation of nucleoside triphosphates derivatized with appropriate tether molecules and their incorporation into RNA or DNA structure by a polymerase reaction.

For several applications, such as for DNA hybridization assays, it is desirable to introduce more than one reporter group to the oligonucleotide structure. This can be performed by three alternative methods: (i) by coupling several base- or carbohydrate-tethered nucleosidic building blocks or nucleoside triphosphates to the growing oligonucleotide chain, (ii) by functionalization of the internucleosidic phosphodiester linkages, or (iii) by using several multifunctional non-nucleosidic building blocks during oligonucleotide chain assembly. All of these methods have their own drawbacks. Since the double helix formation of DNA is based on hydrogen bonding between the complementary base residues, tethers attached to the base moieties often weaken these interactions. This problem is easily overcome by using the tethered nucleosides at the 3'- or 5'-terminus of the coding sequence, or by using labels linked to C5 of pyrimidine residues. Introduction of tethers to the phosphate backbone gives rise to new chiral centers and makes the purification of these analogues difficult. Introduction of the tether arm to the carbohydrate moiety, in turn, often decreases the coupling efficiency of the phosphoramidite due to steric hindrance.

Introduction of linker arms to the nucleobase is most commonly performed by allowing a nucleoside with a good leaving group (N-tosyl, N-benzoyl, halogen, triazole, thiol) at C4 of pyrimidines or C2, C8 or C6 of purines to react with the appropriate nucleophilic linker molecule (e.g. an alkane-$\alpha,\omega$-diamine). Since normally an excess of linker molecule and rather vigorous reaction conditions has to be used laborious purification procedures cannot be avoided. The basic reaction conditions needed gives additional requirements to the other protecting groups in the target molecule. These problems may be overcome by attachment of the linker molecules to C5 of pyrimidine bases by a palladium catalyzed coupling reaction between 5-halogeno pyrimidine nucleoside and an alkynyl- or allyl linker. Recently, attachment of linker arm to the N3 of 3', 5'-O-protected thymidine [*J. Org. Chem.*, 1999, 64, 5083; *Nucleosides, Nucleotides*, 1999, 18, 1339] and 2'-deoxy-5'-O-(4,4'-dimethoxytrityl) uridine [*Org. Lett.* 2001, 3, 2473] based on Mitsunobu reaction have been reported. Since the coupling reaction is performed under mild conditions, a wide range of tethers can be introduced.

The majority of methods described in literature involve attachment of functional groups in the oligonucleotide structure during chain assembly. Hence, introduction of the label molecules has to be performed in solution. In the labeling reaction the amino or mercapto groups of oligonucletides are allowed to react in solution with isothiocyanato, haloacetyl or 2,4,6-triazinyl derivatives of label molecules. Carboxylic acid groups, in turn, can be labeled with amino tethered labels with the aid of water-soluble carbodiimide. Since in all the cases the labeling reaction is performed in aqueous solution with an excess of labeling reactants, laborious purification procedures cannot be avoided. Especially when attachment of several labels is required the isolation and characterization of the desired conjugate is extremely difficult, and often practically impossible. Hence, several attempts to incorporate label molecules or their appropriately protected precursor to oligonucleotide structure during chain assembly have been done [U.S. Pat. No. 4,948,882, U.S. Pat. No. 5,583,236]. The fluorescent label monomers for solid phase chemistry synthesized are most commonly organic dyes (e.g. fluorescein, rhodamine, dansyl, dabsyl, pyrene, Alexa, Cy, TAMRA), several of these blocks are even commercially available. However, such labels and labeled biomolecules suffer from many commonly known drawbacks such as Raman scattering, other fluorescent impurities, low water solubility, concentration quenching etc. In specific binding assays, generally very low concentrations of analytes to be measured are present. Thus multilabeling of oligonucleotides with organic fluorophores may not enhance detection sensitivity the extent needed in many applications. For this type of applications lanthanide(III) chelates are labels of choice since they do not suffer from this phenomenon. In DNA hybridization assays, time-resolved luminescence spectroscopy using lanthanide chelates is well known [Hemmila et al. *Bioanalytical Applications of Labelling Technologies*, Wallac Oy, 1994]. Therefore, a number of attempts have been made to develop new highly luminescent chelate labels suitable for time-resolved fluorometric applications. These include e.g. stabile chelates composed of derivatives of pyridines [U.S. Pat. No. 4,920,195, U.S. Pat. No. 4,801,722, U.S. Pat. No. 4,761,481, PCT/FI91/00373, U.S. Pat. No. 4,459,186, EP Appl.0770610, Remuinan et al, *J. Chem. Soc. Perkin Trans 2*, 1993, 1099], bipyridines [U.S. Pat. No. 5,216,134], terpyridines [U.S. Pat. No. 4,859,777, U.S. Pat. No. 5,202,423, U.S. Pat. No. 5,324,825] or various phenolic compounds [U.S. Pat. No. 4,670,572, U.S. Pat. No. 4,794,191, Ital Pat. 42508 A789] as energy mediating groups and polycarboxylic acids as chelating parts. In addition, various dicarboxylate derivatives [U.S. Pat. No. 5,032,677, U.S. Pat. No. 5,055,578, U.S. Pat. No. 4,772,563] macrocyclic cryptates [U.S. Pat. No. 4,927,923, WO 93/5049, EP-A493745] and macrocyclic Schiff bases [EP-A-369-000] have been published. Also a method for the labeling of a biospecific binding reactant such as hapten, a peptide, a receptor ligand, a drug or PNA oligomer with luminescent labels by using solid-phase synthesis has been published [U.S. Pat. No. 6,080,839, EP 067205A1]. Also oligonucleotide labeling reagents have been synthesized and used in multilabeling of oligonucleotides [*Nucleic Acids Res.*, 22, 1994, *Org. Lett.*, 2001, 3, 2473].

For several applications, such as for those involving an antisense approach, enhanced stability of oligonucleotides towards nucleases is desired. Most commonly this has been achieved by modifying the phosphodiester backbone (mono- and dithioates, phosphoramidites) or carbohydrate moiety.

OBJECTS AND SUMMARY OF THE INVENTION

The object of the present invention is to provide versatile methods for chemical and enzymatic incorporation of tether groups into oligonucleotides, and to improve a recently developed approach for machine assisted oligonucleotide derivatization [*Org. Lett.* 2001, 3, 2473].

The present invention concerns an oligonucleotide labeling reactant, optionally comprising a solid support, of formula (I)

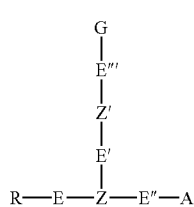

wherein:
R is a temporary protecting group such as 4,4'dimethoxytrityl (DMTr), 4-methoxytrityl (MMTr), trityl (Tr), (9-phenyl)xanthen-9-yl (pixyl) or not present.
A is either a phosphorylating moiety

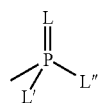

where
L is O, S, or not present
L' is H, $XCH_2CH_2CN$ or XAr, where Ar is phenyl or its substituted derivative, where the substituent is nitro or chlorine, and X is O or S;
L" is $O^-$, $S^-$, Cl, $N(i-Pr)_2$; or A is a solid support, preferably controlled pore glass or polystyrene, tethered to Z via a linker arm E".
Z is a bridge point and is formed from

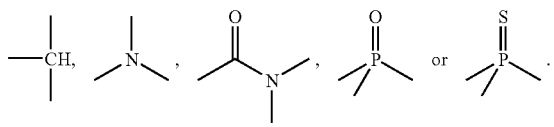

E is a linker arm between R and Z, E' is a linker arm between Z and Z', E" is a linker arm between Z and A and E'" is a linker arm between Z' and G, same or different, and is formed of one to ten moieties, each moiety being selected from the group consisting of phenylene, alkylene containing 1–12 carbon atoms, ethynediyl (—C≡C—), ether (—O—), thioether (—S—), amide (—CO—NH—, —NH—CO—, —CO—NR' and —NR'—CO—), carbonyl (—CO—), ester (—COO— and —OOC—), disulfide (—S—S—), diaza (—N=N—), and tertiary amine (—N—R'), wherein R' represents an alkyl containing less than 5 carbon atoms.
Z' is a purine or pyrimidine base selected from the group consisting of adenine, guanine, cytosine, thymine, uracil, 7-deazaadenine, 7-deazaguanine and hypoxantene, where E' is attached to N1 of pyrimidines and N9 of purines, and E'" is attached to C7 of 7-deazapurines, N3 or C5 of uracil, N3 of thymine, C5 or $N^4$ of cytosine, C8, $N^2$, N3 or $O^6$ of guanine, C8, $N^6$ or C2 of adenine, and where the exocyclic functional groups of said base are appropriately protected preferably with benzoyl, isobutyryl or acetyl, or
Z' is selected from the group consisting of imidazole, pyrazolo[3,4-d]pyrimidine, 4-amino-pyrazolo[3,4-d]pyrimidine, 1,2,4-triazine-3,5-dione, 5-amino-1,2,4-triazine-3-one, where E' is attached to N1 of imidazole, N2 of 1,2,4-triazine-3,5-dione and 5-amino-1,2,4-triazine-3-one, and N7 of 4-amino-pyrazolo[3,4-d]pyrimidine and pyrazolo[3,4-d]pyrimidine, and E" is attached to C4 or C5 of imidazole, C2 or C9 of 4-amino-pyrazolo[3,4-d]pyrimidine, C2, C4 or C9 of pyrazolo[3,4-d]pyrimidine, N4, C5 or C6 of 1,2,4-triazine-3,5-dione and $N^5$ or C6 of $N^5$-amino 1,2,4-triazine-3,5-dione and where the exocyclic functional groups of said base are appropriately protected preferably with benzoyl, isobutyryl or acetyl.
G is a protected bivalent aromatic structure, tethered to two iminodiacetic acid ester groups $N(CH_2COOR")_2$, where R" is an alkyl of 1 to 4 carbon atoms, allyl, ethyltrimethylsilyl, phenyl or benzyl, which phenyl or benzyl can be substituted or unsubstituted, and one of the hydrogen atoms is substituted with E'", and
said bivalent aromatic structure is capable of absorbing light or energy and transferring the excitation energy to a lanthanide ion after said labeling reactant has been deprotected and converted to a lanthanide chelate.
G is alternatively a structure selected from a group consisting of

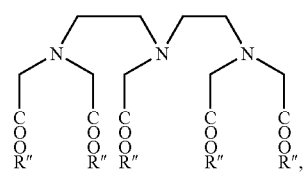

-continued

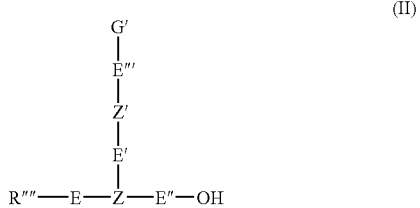

where
R″ is an alkyl of 1 to 4 carbon atoms, allyl, ethyltrimethylsilyl, phenyl or benzyl, which phenyl or benzyl can be substituted or unsubstituted, and one of the hydrogen atoms is substituted with E‴.

G can also be a protected functional group, where the functional group is amino, aminooxy, carboxyl, thiol, and the protecting group is pthaloyl, trityl, 2-(4-nitrophenylsulfonyl)ethoxycarbonyl, fluorenylmethyloxycarbonyl, benzyloxycarbonyl, t-butoxycarbonyl or trifluoroacetuyl for amino and aminooxy, alkyl for carbonyl and alkyl or trityl for thiol.

Alternatively G is a protected or unprotected organic dye, hapten or a spin label.

The present invention also concerns labeling reactants of formula (II)

(II)

$$R''''—E—Z—E''—OH$$

with G′ above Z′ above E‴ above Z (as shown)

wherein:
R″″ is

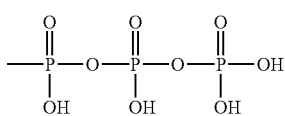

or salts thereof.

Z is a bridge point and is formed from

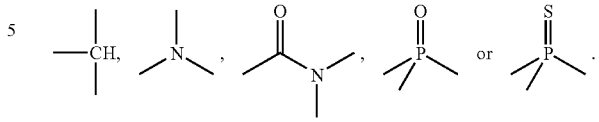

E is a linker arm between R″″ and Z, E′ is a linker arm between Z and Z′, E″ is a linker arm between Z and A and E‴ is a linker arm between Z′ and G′, same or different, and is formed of one to ten moieties, each moiety being selected from the group consisting of phenylene, alkylene containing 1–12 carbon atoms, ethynediyl (—C≡C—), ether (—O—), thioether (—S—), amide (—CO—NH—, —NH—CO—, —CO—NR′— and —NR′—CO—), carbonyl (—CO—), ester (—COO— and —OOC—), disulfide (—S—S—), diaza (—N=N—), amine (—NH—) and tertiary amine (—N—R′), wherein R′ represents an alkyl containing less than 5 carbon atoms.

Z′ is a purine or pyrimidine base selected from the group consisting of adenine, guanine, cytosine, thymine, uracil, 7-deazaadenine, 7-deazaguanine and hypoxantene, where E′ is attached to N1 of pyrimidines and N9 of purines, and E‴ is attached to C7 of 7-deazapurines, C5 of uracil, C5 or $N^4$ of cytosine, C8, $N^2$, N3 or $O^6$ of guanine, C8, $N^6$ or C2 of adenine.

Z′ is alternatively selected from the group consisting of imidazole, pyrazolo[3,4-d]pyrimidine, 4-amino-pyrazolo[3,4-d]pyrimidine, 1,2,4-triazine-3,5-dione, 5-amino-1,2,4triazine-3-one, where E′ is attached to N1 of imidazole, N2 of 1,2,4-triazine-3,5-dione and 5-amino-1,2,4-triazine-3-one, and N7 of 4-amino-pyrazolo[3,4-d]pyrimidine and pyrazolo[3,4-d]pyrimidine, and E″ is attached to C4 or C5 of imidazole, C2 or C9 of 4-amino-pyrazolo[3,4-d]pyrimidine, C2, C4 or C9 of pyrazolo[3,4-d]pyrimidine, N4, C5 or C6 of 1,2,4-triazine-3,5-dione and $N^5$ or C6 of $N^5$-amino 1,2,4-triazine-3,5-dione.

G′ is a bivalent aromatic structure, tethered to two iminodiacetic acid groups $N(CH_2COOH)_2$, or salts thereof, and is chelating a lantanide(III) ion where
one of the hydrogen atoms is substituted with E‴, and
the lantanide(III) (Ln) ion is europium (Eu), samarium (Sm), terbium (Tb), or dysprosium (Dy) and
said bivalent aromatic structure is capable of absorbing light or energy and transferring the excitation energy to said lanthanide ion.

G′ is alternatively a structure selected from a group consisting of

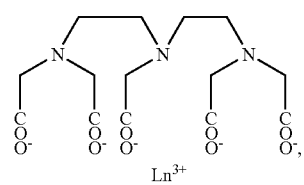

-continued

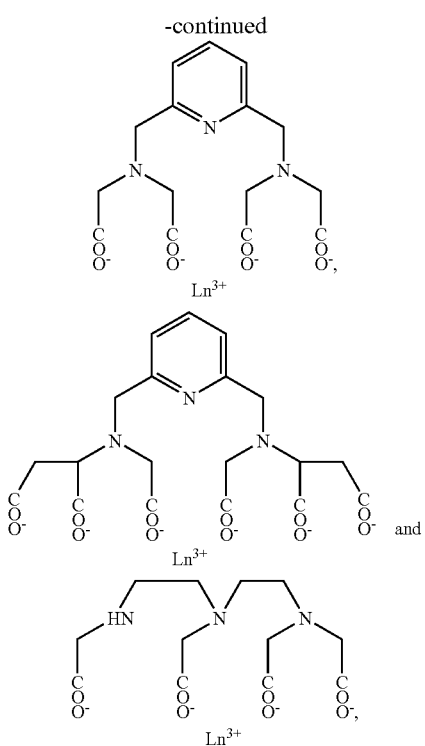

or salts thereof, where
one of the hydrogen atoms is substituted with E''' and
Ln is Eu, Tb, Sm or Dy.

G' can also be a functional group, where the functional group is amino, aminooxy, carboxyl, thiol, Alternatively G is a organic dye, hapten or a spin label.

The invention further concerns an oligonucleotide or polynucleotide conjugate comprising a label that can be synthesized using a labeling reactant of formula (I) or formula (II). The conjugate comprises a coding sequence consisting of a natural DNA and/or RNA fragment or its monothioate, dithioate or phosphoramidate analogue, or a PNA oligonucleotide, or their mixture. Said label one or several, same or different, obtained, after i) introduction of said labeling reactant,
ii) introduction and deprotection of said labeling reactant,
iii) introduction and deprotection of said labeling reactant followed by introduction of a lanthanide(III) ion when the label is a luminescent or non-luminescent lanthanide(III) chelate, or
iv) introduction and deprotection of said labeling reactant followed by introduction of a signaling moiety in solution as its thiocyanate, active ester, dichlorotriazine, aldehyde, ketone, or haloacetamido derivative when said labeling reactant comprises a deprotected functional group, is attached to the 3'- or/and 5'-terminus of the oligonucleotide chain or/and within the coding sequence.

The Major Advantages and Key Steps of Oligonucleotide Derivatization Using Labeling Reactants and/or Conjugates According to the Invention The present invention for oligonucleotide derivatization combines several important features:

(i) The previously developed synthetic strategy for the preparation of nucleosidic oligonucleotide labeling reactants can be exploited.

(ii) The labeling reactants synthesized are solids. Hence their storage and handling do not suffer from the problems associated with oily non-nucleosidic phosphoramidites.

(iii) Since the building blocks are derivatives of acyclic nucleosides bearing a tether arm attached to the base moiety, they can in high efficiency be coupled to the oligonucleotide chain using standard protocols.

(iv) Since the tether arm is attached to the base moiety, multilabeling of oligonucleotides can be achieved.

(v) If a ligand structure/structures is/are incorporated to the oligonucleotide chain during chain assembly, it/they can be converted to the corresponding lanthanide(III) chelate(s) using slightly modified deprotection steps. Hence laborious solution phase labeling as well as synthesis of the activated chelates and oligonucleotides tethered to functional groups can be avoided.

(vi) For the preparation of 3'-tethered oligonucleotides the ligand structures can be converted also to the corresponding solid supports that can be used in solid phase oligonucleotide synthesis.

(vii) The labeling reactants can also be converted to corresponding triphosphates and incorporated into the biomolecule structure using polymerases. Since the molecules do not terminate chain elongation, several of them should allow multilabeling of biopolymers.

(viii) The oligonucleotide an polynucleotide conjugates synthesized with the aid of these labeling reactants have enhanced stability towards nucleases.

BRIEF DESCRIPTION OF THE DRAWINGS

FIG. 1a is the observed mass spectrum, and FIG. 1b is the molecular ion after deconvolution. M- (obs.) 7921.6, M- (calc.). 7922.0.

DETAILED DESCRIPTION OP THE INVENTION

Figure 1:
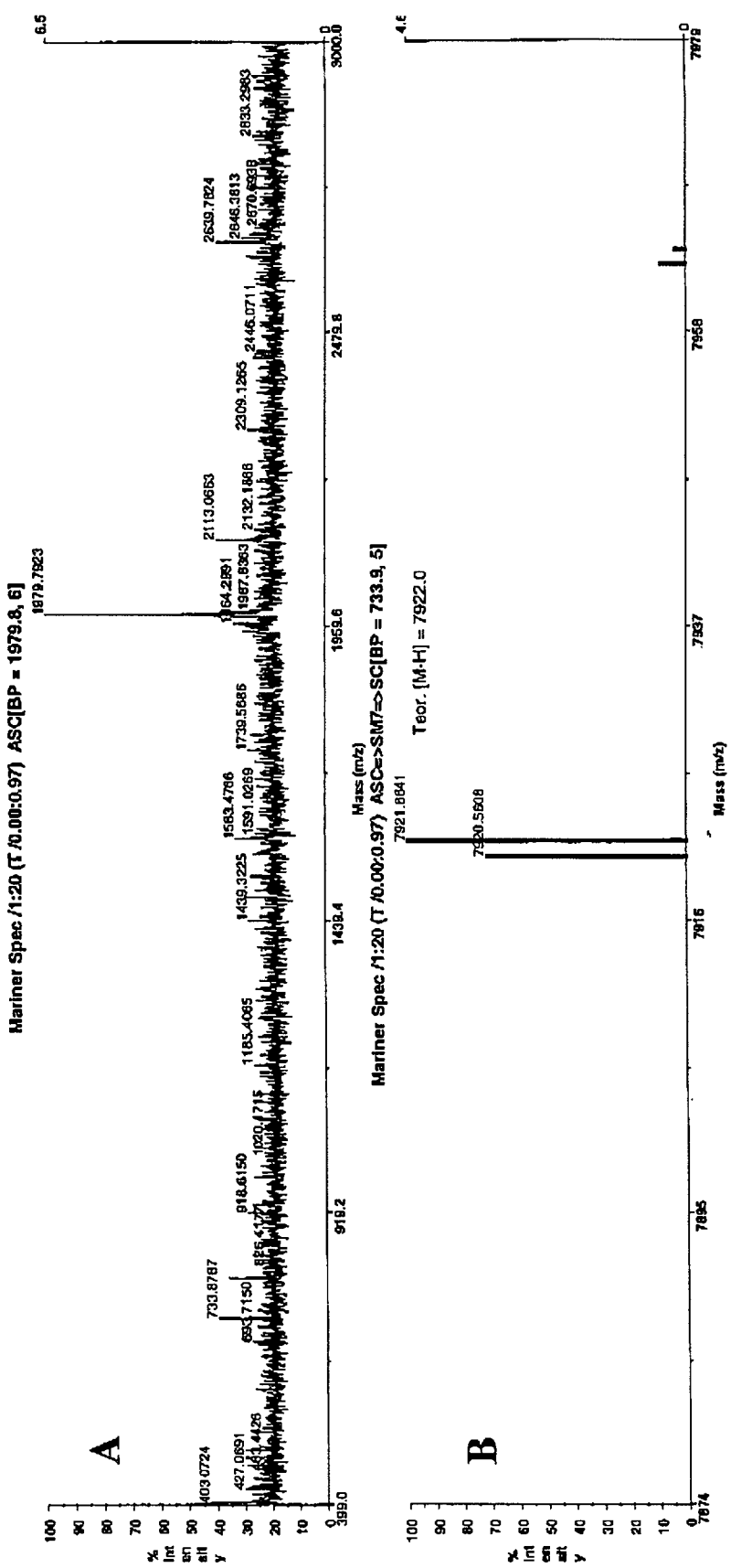
FIG. 1 shows ESI-TOF (Electron Spray Ionization Time Of Flight) mass spectrum (negative detection mode) of an oligonucletide conjugate 5'-X5-GTTCTTCTTGGAGTAA-3' synthesized using labeling reactant 11, after deprotection, introduction of the europium(III) ion and reversed phase HPLC purification.

The present invention improves the recently developed approach for oligonucleotide derivatization [*Org. Lett.* 2001, 3, 2473]. The approach of the invention differs from the disclosed approach referred to in that an optically pure alcohol replaces the carbohydrate moiety while the base moiety is unchanged. Due to the lack of a carbohydrate moiety the oligonucleotide probes have enhanced stability towards nucleases [*Nucleic Acids Res.* 1991, 19, 2587]. For some applications, such as DNA-hybridization assays, it is desirable that the labeled part does not hybridize with the target sequence. For these types of applications the labels are attached to the 3'- or 5'-terminus of the coding sequence. Furthermore, the labeling reactant is designed to have minimal hybridization properties, i.e. the label is attached to base moieties at positions needed for Watson-Crick base pairing, and the alcohol moiety of the labeling reactants is designed to decrease the melting temperature of a possible dublex at the point of labeling. In applications where labeling is needed within the target sequence, the signaling moiety is attached to nucleobases not necessary for base pairing (e.g. C5 of pyrimidines) and the alcohol moiety is designed not to diminish the melting temperature [*Nucleic Acids Res.* 1991, 19, 2587]. This type of labeling reagents can also be converted to corresponding triphosphates and incorporated into the oligo- or polynucleotide structure using a polymerase reaction.

In contrast to several commercially available non-nucleosidic oligonucleotide building blocks, the oligonucleotide labeling reactants of this invention are solid materials.

The labeling reactants of the present invention are particularly suitable for the preparation of oligonucleotide conjugates bearing several functional groups or label molecules in their structure. A preferable alternative for G is a protected functional group, and for G' a functional group, said functional group being preferably amino, carboxyl, aminooxy or thiol.

Another preferred alternative for G and G' is an organic dye or a spin label. Preferable organic dyes are dabsyl, dansyl, fluorescein, rhodamine, Alexa, Cy or TAMRA.

Yet another preferable alternative for G and G' is a hapten, especially biotin, dinitrophenol or digoxigenin.

A particularly preferable transient protecting group R is 4,4'-dimethoxytrityl.

The term 'bivalent' in the definition of G and G' shall mean a chemical group bound to two neighboring atoms. The bivalent aromatic structure G and G' is preferably selected from a group consisting of carbostyryl or structures disclosed in Scheme 1.

The substituent R''' is preferably methyl, ethyl or allyl.

Most preferably, the labeling reactant is
(S)-1-[3-(4,4'-dimethoxytrityl-2,3-dihydroxypropyl)-3-O-(2-cyanoethyl N,N-diisopropyl)phosphoramidato)-3-(N6-trifluoroacetamidohexyl)uracil,
(S)-1-[3-(4,4'-dimethoxytrityl-2,3-dihydroxypropyl)-2-O-(2-cyanoethyl N,N-diisopropyl)phosphoramidato)]-1-{(tetramethyl 2,2',2'',2'''-[(4-(hex-5-yn-1-yl)pyridine-2,6-diyl)bis(methylene-nitrilo)]tetrakis(acetato)uracil,
(S)-1-[3-(4,4'-dimethoxytrityl-2,3-dihydroxypropyl)-2-O-(2-cyanoethyl N,N-diisopropyl)phosphoramidato)]-1-[3-(2,2',2'',2'''-{[4'-(4''-(5-hexyn-6-yl)phenyl)-2,2':6',2''-terpyridine-6,6''-diyl]bis(methylenenitrilo)}tetrakis(acetato)uracil or
(S)-1-[(3,4-dihydroxybutyl-4-O-(4,4'-dimethoxytrityl)-3-O-(2-cyanoethyl N,N-diisopropyl)phosphoramidato]-1-(5-hydroxypthalimidohexyn-1-yl uracil).

Labels preferable for multilabeling are non-luminescent or luminescent lanthanide(III) chelates. The lanthanide chelate is preferably europium(III), terbium(III), samarium(III) or dysprosium(III) chelate.

The invention is further elucidated by the following examples. The structures and synthetic routes employed in the experimental part are depicted in schemes 2–6. Scheme 2 illustrates the synthesis of the labeling reagents 6. The experimental details are given in examples 1–5 and 16. Scheme 3 illustrates the synthesis of the labeling reagent 11. The experimental details are given in examples 6–9 and 16. Scheme 4 illustrates the synthesis of the labeling reagent 13. The experimental details are given in examples 10 and 16. Scheme 5 illustrates the preparation of a labeling reagent 19. Experimental details are given in examples 11–16. Scheme 6 illustrates the method for the introduction of lanthanide (III) chelates to the oligonucletide structure using labeling reactant 6. Experimental details are given in example 17. Scheme 7 illustrates the method for the introduction of lanthanide(III) chelates to the oligonucletide structure using labeling reactant 11. Experimental details are given in example 18. Example 19 describes principles of oligonucletide purification with HPLC techniques. Scheme 8 describes the synthetic route for the preparation of an acyclic nucloside triphosphate which allows enzymatic incorporation of lantanide(III) chelates to a polynucleotide structure.

Experimental Procedures

Reagents for machine assisted oligonucleotide synthesis were purchased from Applied Biosystems (Foster City, Calif.). 2-Cyanoethyl-N,N,N,N',N'-tatraisopropylphosphodiamidite, N6-trifluoroacetamidohexanol and 3-benzoyluracils were synthesized using literature procedures. Adsorption column chromatography was performed on columns packed with silica gel 60 (Merck). NMR spectra were recorded on a Brucker 250 instrument operating at 250.13 MHz for $^1$H, or a Jeol LA-400 spectrometer operating at 161.9 MHz for $^{31}$P. Me$_4$Si was used as an internal ($^1$H) and H$_3$PO$_4$ as an external reference ($^{31}$P). Coupling constants are given in Hz. Mass spectra were recorded on a VG ZabSpecao TOF (EI) and Perseptive Biosystems Mariner (ESI-TOF) instruments. Oligonucleotides were assembled on an Applied Biosystems Expedite Synthesizer using phosphoramindite chemistry and recommended protocols (DMTr-Off-synthesis).

EXAMPLE 1

The synthesis of (S)-1-(2,3-O-isopropylidene-2,3 dihydroxypropyl-3-benzoyluracil (1)

N3-Benzoyluracil (4.0 g, 18.5 mmol), S-solketal (3.2 g, 24.0 mmol) and triphenylphosphine (5.80 g, 22.0 mmol) were dissolved in dry THF (40 mL). Diethylazodicarboxylate (3.50 mL; 22.0 mmol) was added in five portions during 15 min, and the mixture was stirred at room temperature for additional 2 h. After concentration in vacuo the product was purified on silica gel (eluent diethyl ether). Yield was 5.3 g (86%). $^1$H NMR (CDCl$_3$) δ: 7.94 (1H, d, J 7.5); 7.66 (1H, m); 7.45 (2H, m); 7.35 (2H, d, J 8.1); 5.5.82 (1H, d, J 7.5); 4.38 (1H, m); 4.07 (2H, m); 3.71 (2H, m); 1.46 (3H, s); 1.35 (3H, s).

EXAMPLE 2

The synthesis of (S)-1-(2,3-O-isopropylidene-2,3-dihydroxypropyluracil (2)

Compound 1 (6.8 g) was suspended sat aq. ammonia and stirred at ambient temperature for 2 h after being concentrated in vacuo and purified on silica gel (eluent 5% methanol in dichloromethane v/v). $^1$H NMR (CDCl$_3$) δ: 9.77 (1H, br); 7.84 (1H, d, J 5); 5.72 (1H, d, J 5); 4.40 (1H, m); 411 (2H, m); 3.73 (2H, m); 1.43 (3H, s); 1.34 (3H, s). (MS, EI$^+$) 226. The purified compound contained 1 eq of benzamide, as judged on $^1$H NMR and MS analyses. Benzamide: $^1$H NMR (CDCl$_3$) δ: 7.48 (3H, m); 7.32 (2H, d, J 8); 6.13 (2H, br); (MS, EI$^+$) 121.

EXAMPLE 3

The synthesis of (S)-1-(2,3-O-isopropylidene-2,3-dihydroxypropyl-3-(N6-trifluoroacetamido-hexyl) uracil (3)

Compound 2 (2.50 g, 11.05 mmol); N6-trifluoroacetamidohexan-1-ol (2.6 g, 12.16 mmol) and triphenylphosphine (3.19 g, 12.16 mmol) were suspended in dry THF (20 mL). DEAD (1.92 mL) was added in four portions during 15 min, and the mixture was allowed to stir overnight at ambient temperature. After concentration purification was performed on silica gel (eluent 3% methanol in dichloromethane v/v). $^1$H NMR (CDCl$_3$) δ: 7.27(1H, d, J 7.9); 6.69 (br t); 5.73 (1H, d, J 7.9); 4.38 (1H, m); 4.11 (2H, m); 3.94 (2H, t, J 7.0); 3.69 (2H, m); 3.35 (2H, q, J 6.4); 1.66 (4H, m); 1.42 (3H, s); 1.40 (4H, m); 1.34 (3H, s).

EXAMPLE 4

The synthesis of (S)-1-(2,3-dihydroxypropyl-3-(N6-trifluoroacetamidohexyl)uracil (4)

Compound 3 was dissolved in methanol containing iodine (1% w/v), and the mixture was stirred overnight at room temperature. The excess of iodine was destroyed by addition of solid sodium thiosulfate. After filtration and concetration the product was isolated on silica gel (eluent 10% methanol in dichloromethane v/v). $^1$H NMR (CDCl$_3$) δ: 7.28 (1H, d, J 7.8); 6.82 (1H, br t); 5.73 (1H, d, J 7.8); 4.00 (2H, m); 3.95 (2H, t, J 7.0); 3.80 (1H, m); 3.59 (2H, ma); 3.35 (2H, q, J 6.4); 1.62 (4H, m); 1.37 (4H, m).

EXAMPLE 5

The synthesis of (S)-1-[3-(4,4'-dimethoxytrityl-2,3-dihydroxypropyl)]-3-(N6-trifluoroacetamido-hexyl) uracil (5).

Compound 4 was dried by coevaporation with dry pyridine and dissolved in the same solvent. 4,4'-Dimethoxytrityl chloride and catal. DMAP were added and the mixture was strirred 2 h at ambient temperature and concentrated. The residue was dissolved in dichloromethane, washed with NaHCO$_3$, dried over Na$_2$SO$_4$ and concentrated. Purification on silica (eluent diethyl ether) yielded the title compound as a solid. $^1$H NMR (CDCl$_3$) δ: 7.26 (9H, m); 7.13 (1H, d, J 7.9); 6.83 (4H, d, J 8.9); 6.69 (1H, br); 5.61 (1H, d, J 7.9); 4.05 (2H, m); 3.89 (2H, t, J 7.0); 3.79 (6H, s); 3.68 (1H, m); 3.33 (2H, q, J 6.7); 3.18 (2H, d, J 5.2); 1.78 (1H, br); 1.60 (2H, m); 1.36 (2H, m).

EXAMPLE 6

The synthesis of (S)-1-(2,3-O-isopropylidene-2,3-dihydroxypropyl-3-(6-hexyn-5-yl)uracil (7)

Compound 2 (2.50 g, 11.05 mmol); 5-hexyn-1-ol (n mL; 12.16 mmol) and triphenylphosphine (3.19 g, 12.16 mmol) were suspended in dry THF (20 mL). DEAD (1.92 mL) was added in four portions during 15 min, and the mixture was allowed to stir overnight at ambient temperature. After concentration purification was performed on silica gel (eluent 3% methanol in dichloromethane v/v). $^1$H NMR (CDCl$_3$) δ: 7.26(1H, d, J 8.1); 5.73 (1H, d, J 8.1); 4.38 (1H, in); 4.11 (2H, m); 3.96 (2H, t, J 7.0); 3.69 (2H, m); 2.80 (2H, br); 2.25 (2H, td, J 2.7 and 7.1); 1.95 (1H, t, J 2.7); 1.76 (2H, m); 1.61 (2H, m); 1.42 (3H, s); 1.34 (3H, s). MS (EI$^+$) 306.

EXAMPLE 7

The synthesis of (S)-1-(2,3-O-isopropylidene-2,3-dihydroxypropyl-3-(6-hexyn-5-yl)uracil (8).

Compound 6 was deprotected and purified as described in Example 4. $^1$H NMR (CDCl$_3$) δ: 7.27 (1H, d, J 7.9); 5.74 (1H, d, J 7.9); 3.99 (2H, m); 3.96 (2H, t, J 7.3); 3.84 (1H, m); 3.61 (2H, m); 2.84 (2H, br); 2.25 (2H dt, J 2.7 and 7.0); 1.95 (1H, t, J 2.7); 1.75 (2H, m); 1.60 (1H, m).

EXAMPLE 8

The synthesis of (S)-1-[3-(4,4'-dimethoxytrity-2,3-dihydroxypropyl)]-3-(hex-5-yn-1-yl)uracil (9).

Compound 7 was dimethoxytritylated and purified using methods described in Example 5. $^1$H NMR (CDCl$_3$) δ: 7.30 (9H, m); 7.22 (1H, d, J 7.9); 7.17 (4H, d, J 9.0); 5.74 (1H, d, J 7.9); 3.98 (4H, m); 3.94 (1H, m); 3.80 (6H, s); 2.45 (1H, br); 2.23 (2H, dt, J 2.7 and 7.2); 1.95 (1H, t, J 2.7); 1.76 (2H, m); 1.57 (2H, m).

EXAMPLE 9

The synthesis of (S)-1-[3-(4,4'-dimethoxytrityl-2,3-dihydroxypropyl)]-3-{tetramethyl 2,2',2",2"'-[(4-(hex-5-yn-1-yl)pyridine-2,6-diyl)bis(methylenenitrilo)}-tetrakis(acetato)uracil (10).

A mixture of tetramethyl 2,2',2",2"'-[4-bromopyridine-2,6-diyl)bis(methylenenitrilo)-tetrakis(acetate) and compound 9 in dry THF and triethylamine was deaerated with argon. Bis(triphenylphosphinepalladium(II) chloride and CuI were added and the mixture was stirred for 7 h at 55° C. The cooled solution was filtered, the filtrate was evaporated and redissolved in dichloromethane. The solution was washed with water, dried and concentrated. Purification on silica gel yielded the title compound as a solid (75%). $^1$H NMR (CDCl$_3$) δ: 7.39 (2H, s); 7.27 (9H, m); 7.12 (1H, d, J 7.9); 6.83 (4H, d, J 8.8); 5.61 (1H, d, J 7.9); 4.11 (2H, m); 3.98 (4H, s); 3.94 (1H, m); 3.79 (6H, s); 3.70 (12H, s); 3.61 (8H, s); 3.17 (2H, d, J 4.9); 2.74 (1H, br); 2.44 (2H, t, J 7.1); 1.72 (2H, m); 1.65 (2H, m).

EXAMPLE 10

The synthesis of (S)-1-[3-(4,4'-dimethoxytrityl-2,3-dihydroxypropyl)]-3-(2,2',2",2"'-{[4'-(4"-(5-hexyn-6-yl)phenyl)-2,2':6',2"-terpyridine-6,6"-diyl]bis(methylenenitrilo)}tetrakis(acetato)uracil (12).

A mixture of tetramethyl 2,2',2",2"'-{([4'-(4'-bromophenyl)-2,2':6',2"-terpyridine-6,6"-diyl]bis(methylenenitrilo) }tetrakis(acetate) and compound 9 in dry THF and triethylamine was deaerated with argon. Bis (triphenylphosphinepalladium(II) chloride and CuI were added and the mixture was stirred for 7 h at 55° C. The cooled solution was filtered, the filtrate was evaporated and redissolved in dichloromethane. The solution was washed with water, dried and concentrated. Purification on silica gel yielded the title compound as a solid (75%). $^1$H NMR (DMSO-d$_6$): δ: 8.63 (2H, s); 8.55 (2H, d, J 7.7); 8.02 (2H, t, J 7.7); 7.86 (2H, t, J 8.5); 7.62 (4H, t, J 7.3); 7.53 (1H, d, J 8.1); 7.42 (2H, d, J 7.4); 7.28 (4H, m); 6.88 (4H, d, J 8.8); 5.64 (1H, d, J 7.7); 5.32 (1H, d, J 5.5); 4.10 (4H, s); 3.86 (2H, m); 3.72 (8H, s); 3.68 (6H, s); 3.51 (1H, m); 2.97 (2H, m); 2.88 (2H, m); 2.51 (6H, m).

EXAMPLE 11

The synthesis of (S)-1-(3,4-O-isopropylidene-3,4-dihydroxybutyl)-3-benzoyl-5-iodouracil (14)

The title compound was synthesized using procedures described in Example 1 by Mitsunobu reaction between 3-benzoyl-5-iodouracil and (S)-1,2-O-isopropylidene-1,2,4-butanetriol. $^1$H NMR (CDCl$_3$): δ 7.92 (2H, d); 7.82 (1H, s);

7.67 (1H, t); 7.50 (2H, d); 4.09 (tot 3H, m); 3.89 (1H, m); 3.56 (1H, m); 2.04 (1H, m); 1.87 (1H, m); 1.44 (3H, s); 1.38 (3H, s).

EXAMPLE 12

The synthesis of (S)-1-(3,4-dihydroxybutyl)-3-benzoyl-5-iodouracil (15)

Compound 14 (1.17 g) was suspended in 80% aqueous acetic acid (15 mL) and stirred overnight at 50° C. All volatile material was removed in vacuo. The residue was dissolved in methylene chloride, washed with sat. $NaHCO_3$, dried and concentrated. Purification on silica gel (eluent 10% MeOH in $CH_2Cl_2$) yielded the title compound as a solid. $^1H$ NMR ($CDCl_3$): δ 7.92 (2H, d); 7.83 (1H, s); 7.68 (1H, t); 7.51 (2H, d); 3.99 (2H, m); 3.69 (2H, m), 3.48 (1H, m); 1.90 (1H, m); 1.78 (1H, m).

EXAMPLE 13

The synthesis of (S)-1-(3,4-dihydroxybutyl)-5-iodouracil (16)

Debenzoylation of compound 15 as described in Example 2 yielded compound 16. It was used for the next step without further characterization.

EXAMPLE 14

The synthesis of (S)-1-[(3,4-dihydroxybutyl-4-O-(4,4'-dimethoxytrityl)]-5-iodouracil (17)

Dimethoxytritylation of compound 16 using procedure described in Example 3 gave compound 17. $^1H$ NMR ($CDCl_3$): δ 7.67 (1H, s); 7.26 (9H, m); 6.83 (4H, d, J 8.9) 3.87 (2H, m); 3.79 (6H, s); 3.72 (3H, m); 3.14 (2H, m); 3.09 (1H, br); 1.71 (1H, m); 1.66 (1H, m).

EXAMPLE 15

The synthesis of (S)-1-[(3,4-dihydroxybutyl-4-O-(4,4'-dimethoxytrityl)]-5-(hydroxypthalimidohexyn-1-yl)uracil (18)

Yogishawa reaction between trifluoroacetamidoprorargylamine and Compound 17 using procedures described in Example 9 yielded the title compound as a solid.

EXAMPLE 16

Synthesis of the Phosphoramidites. General Procedure

Predried alcohol and 2-cyanoethyl N,N,N',N'-tetraisopropylphosphordiamidite (1.5 eq) were dissolved in dry acetonitrile. 1H tetrazole (1 eq; 0.45 M in acetonitrile) was added, and the mixture was stirred for 30 min at room temperature before being poured into 5% $NaHCO_3$ and extracted with dichloromethane and dried over $Na_2SO_4$. Purification was performed on silica gel column (eluent petr. ether: ethyl acetate: triethyamine; 2:5:1, v/v/v).

(S)-1-[3-(4,4'-dimethoxytrityl-2,3-dihydroxypropyl)-3-O-(2-cyanoethyl N,N-diisopropyl)phosphoramidato)-3-(N6-trifluoroacetamidohexyl)uracil (6). $^{31}P$ NMR: δ 152.46 (0.5 P); 152.30 (0.5 P).

(S)-1-[3-(4,4'-dimethoxytrityl-2,3-dihydroxypropyl-2-O-(2-cyanoethyl N,N-diisopropyl) phosphoramidato)]-1-{tetramethyl 2,2',2",2'"-[(4-(hex-5-yn-1-yl)pyridine-2,6-diyl) bis(methylene-nitrilo)}tetrakis(acetato)uracil (11). $^{31}P$ NMR: δ 152.65 (0.5 P); 152.47 (0.5 P).

(S)-1-[3-(4,4'-dimethoxytrityl-2,3-dihydroxypropyl)-2-O-(2-cyanoethyl N,N-diisopropyl)phosphoramidato)]-1-[3-(2,2',2",2'"-{[4'-(4"-(5-hexyn-6-yl)phenyl)-2,2':6', 2"-terpyridine-6,6"-diyl]bis(methylenenitrilo)}tetrakis (acetato)uracil (13).
$^{31}P$ NMR: δ 152.97 (0.5 P); 152.81 (0.5 P).

(S)-1-[(3,4-dihydroxybutyl-4-O-(4,4'-dimethoxytrityl)-3-O-(2-cyanoethyl N,N-diisopropyl)phosphoramidato]-1-(5-hydroxypthalimidohexyn-1-yluracil) (19).
$^{31}P$ NMR: δ 152.85 (0.5 P); 152.74 (0.5 P).

EXAMPLE 17

Introduction of Primary Amino Groups to an Oligonucleotide Structure Using Compound 6 and Labeling of Amino Functions with a Non-Luminescent Europium(III) Chelate Model sequences were synthesized on an ABI instrument, and up to 10 phosphoramidites 6 were coupled to its 5'-terminus using standard conditions (concentration 0.2 M in acetonitrile; coupling time 60 s). No difference in coupling efficiency between 6 and normal nucleosidic building blocks were detected as judged on DMTr-cation response. After standard ammoniolytic deprotection, the oligonucleotide prepared was isolated on PAGE and desalted on NAP columns. This oligonucleotide was finally labeled with a non-luminescent europium(III) chelate as described by Dahlen et al. *Bioconjugate Chem.*, 1994, 5, 268.

EXAMPLE 18

Introduction of Lanthamide(III) Chelates to an Oligonucletide Structure Using Compound 11

Model sequences were synthesized as described above. One or five phosphoramidites 11 were coupled to its 5'-terminus using standard conditions. No difference in coupling efficiency between 11 and normal nucleosidic building blocks were detected. When the chain assembly was completed, the oligonucleotides were deprotected by first treating the solid support with 0.1 M sodium hydroxide for 4 h at ambient temperature. 1.0 M ammonium chloride was then added, and the solution was concentrated in vacuo. The residue was treated with conc. ammonia for 16 h at 60° C., after which europium citrate (10 eq. per ligand) was added, and the mixture was kept 90 min at room temperature. Desalting by NAP followed by RP HPLC yielded the desired oligonucleotide conjugates containing one or five europium (III) chelates in their structure.

EXAMPLE 19

Purification of Oligonucletide Conjugates on HPLC

The oligonucletide conjugates were purified on reversed phase techniques using either HyPURITY™ Elite (ThermoQuest), Purospher RP-18e (Merck) or Inertsil ODS-3 (GL Sciences) columns and TEAA buffer and acetonitrile gradients as mobile phase.

SCHEME 1
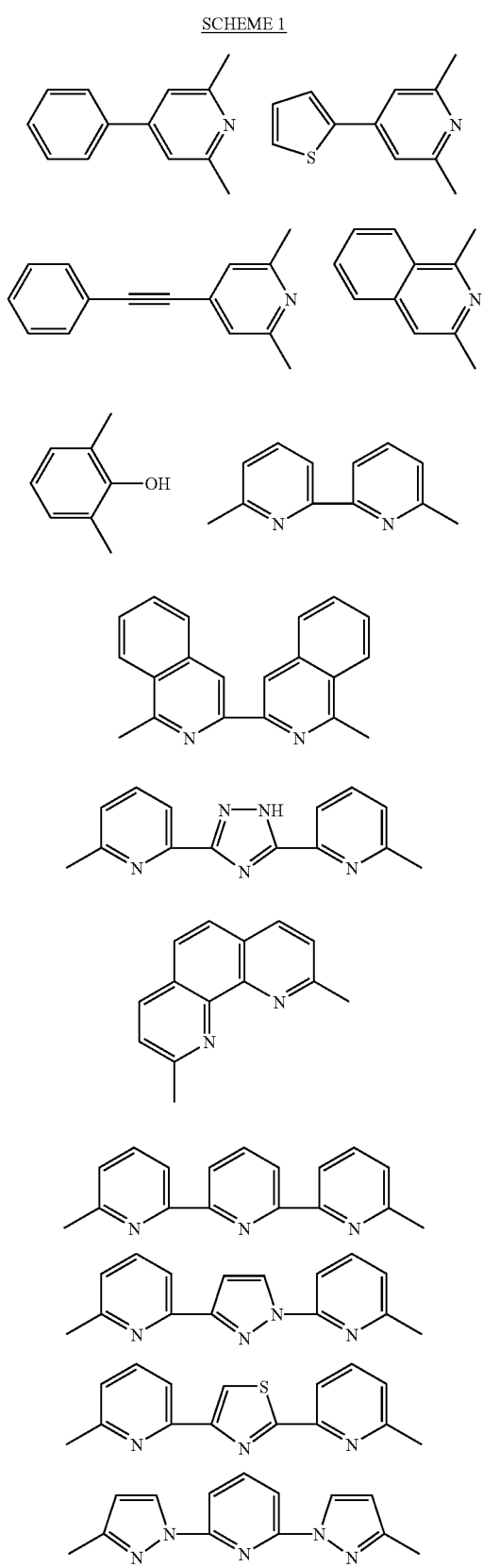
-continued
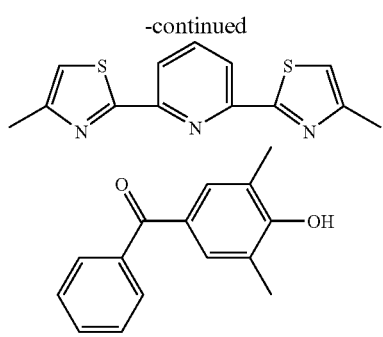
SCHEME 2
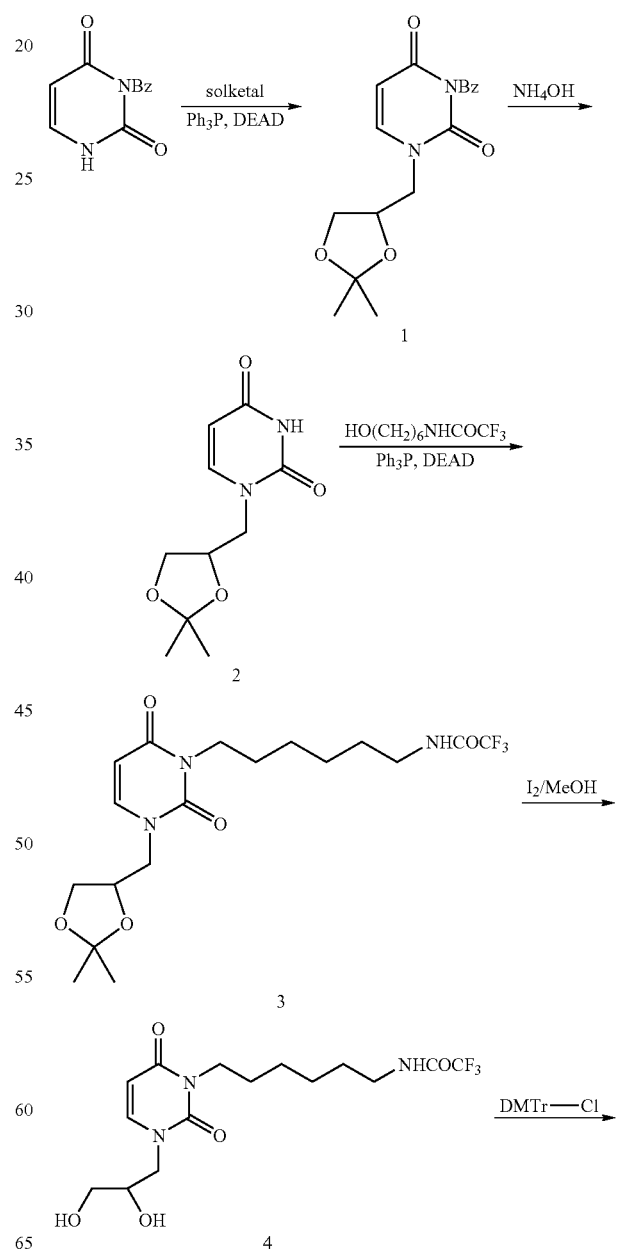

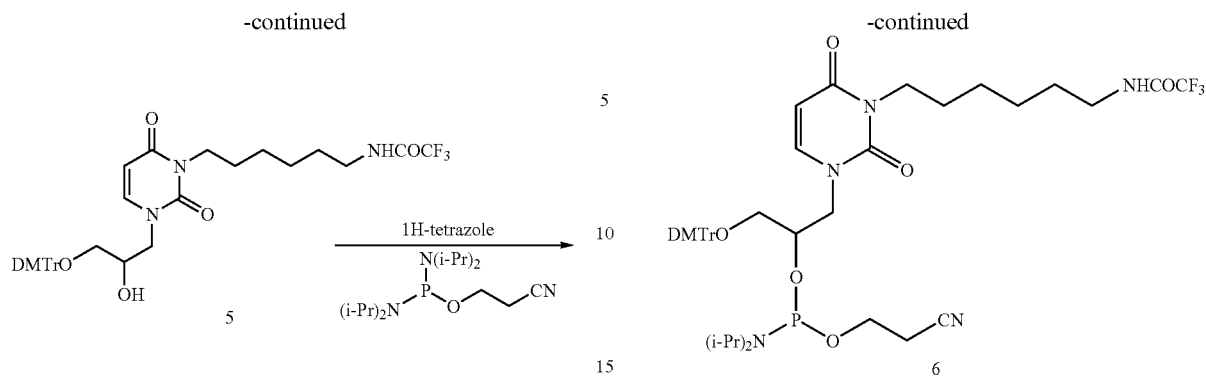
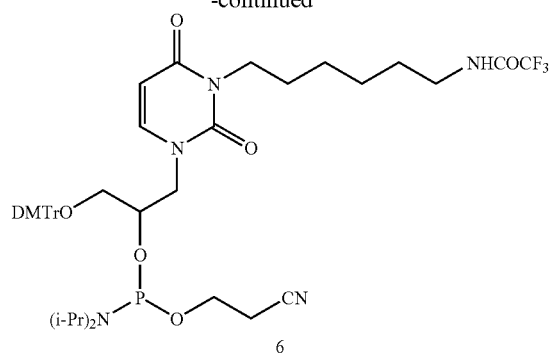
SCHEME 3
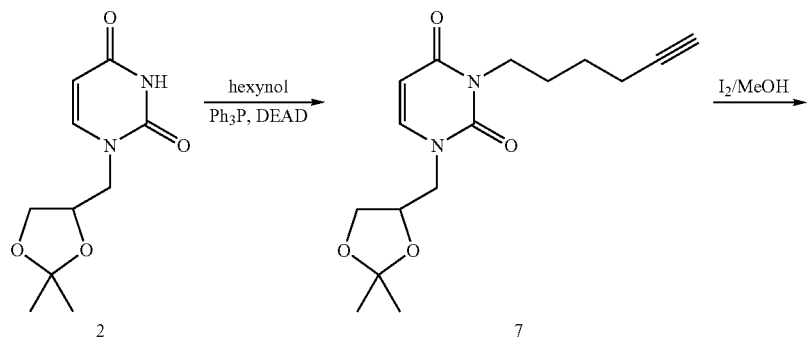
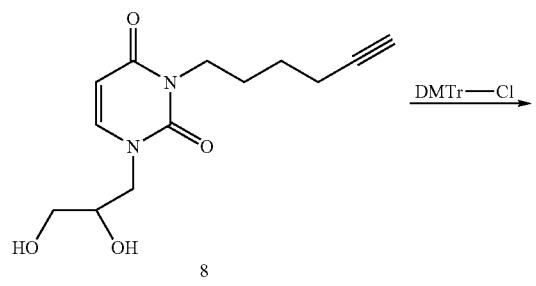
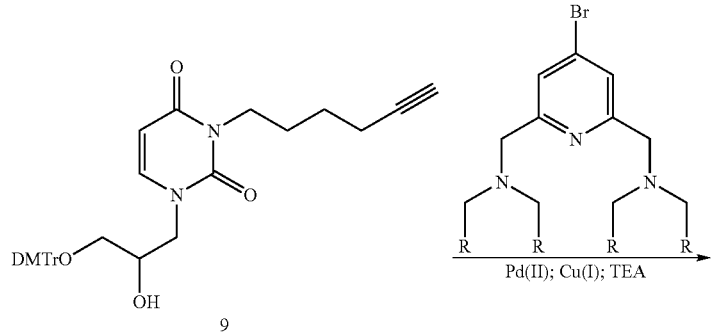

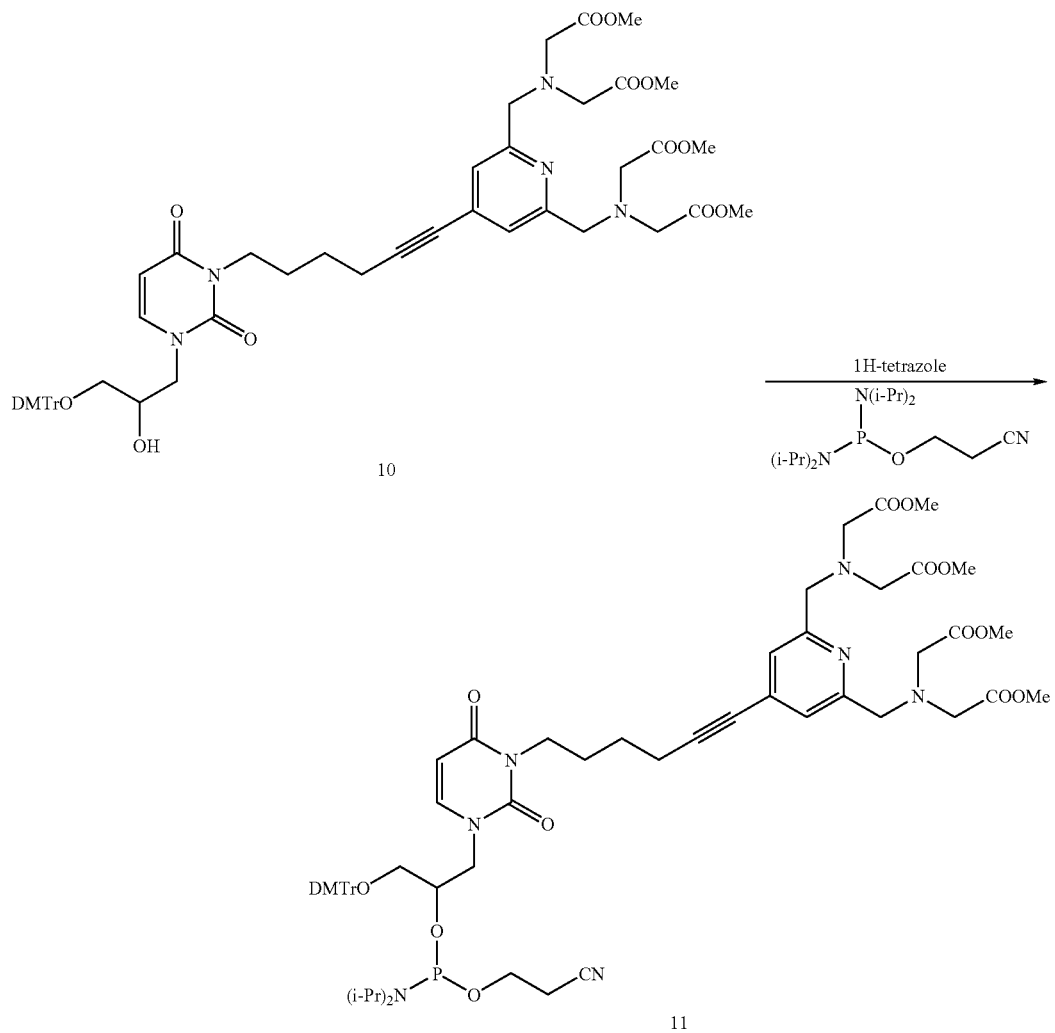
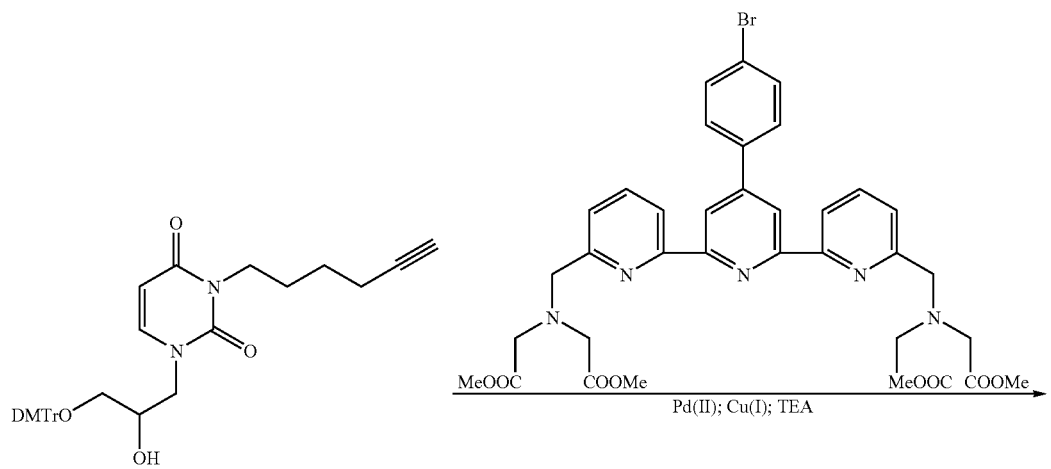
SCHEME 4

-continued
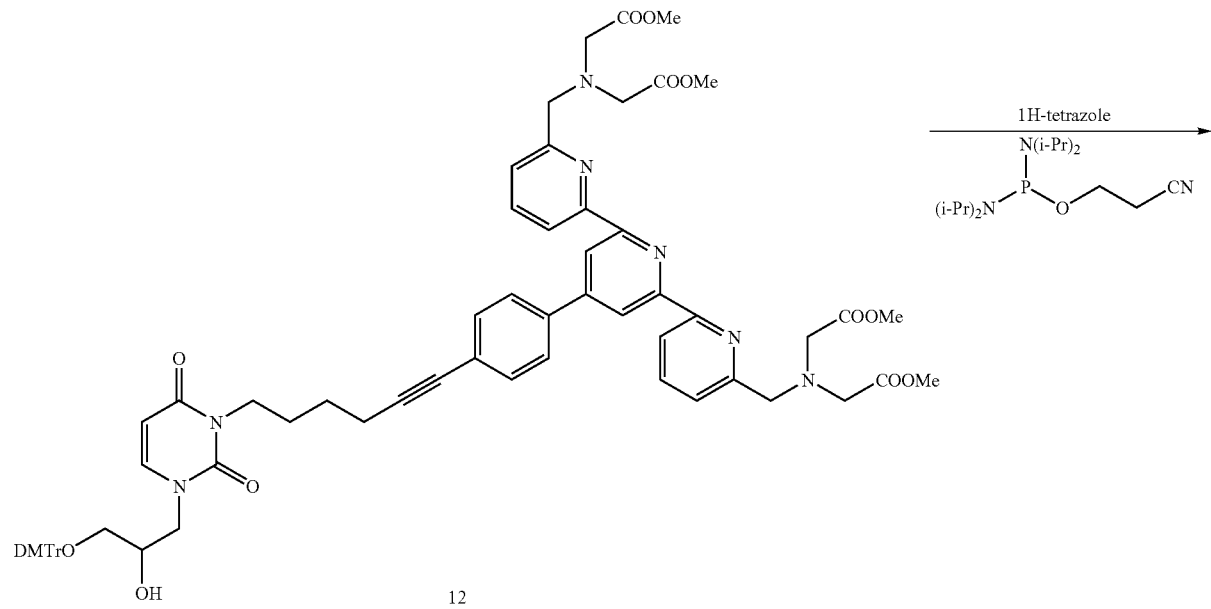
12
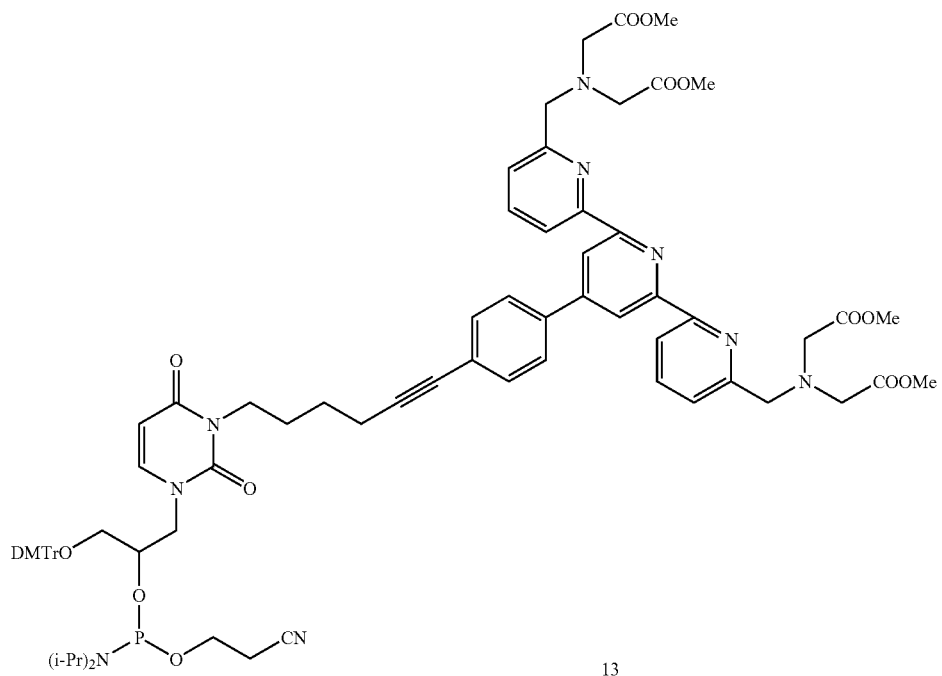
13

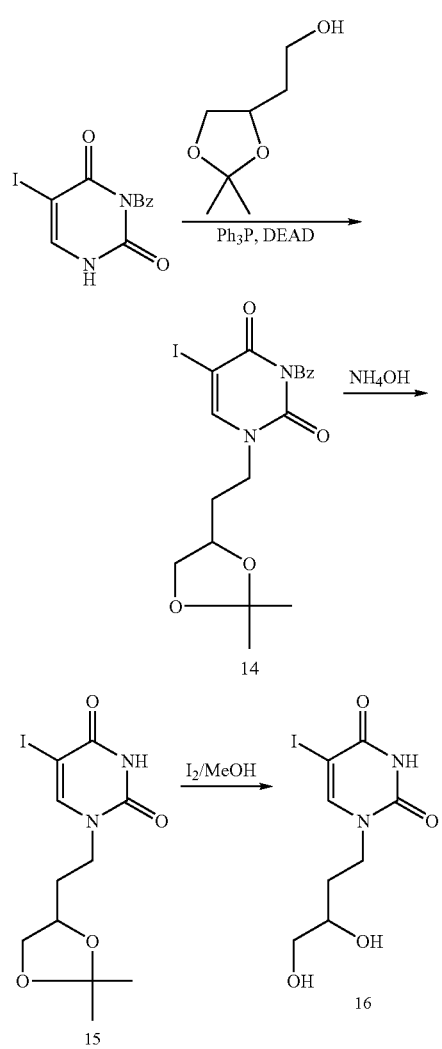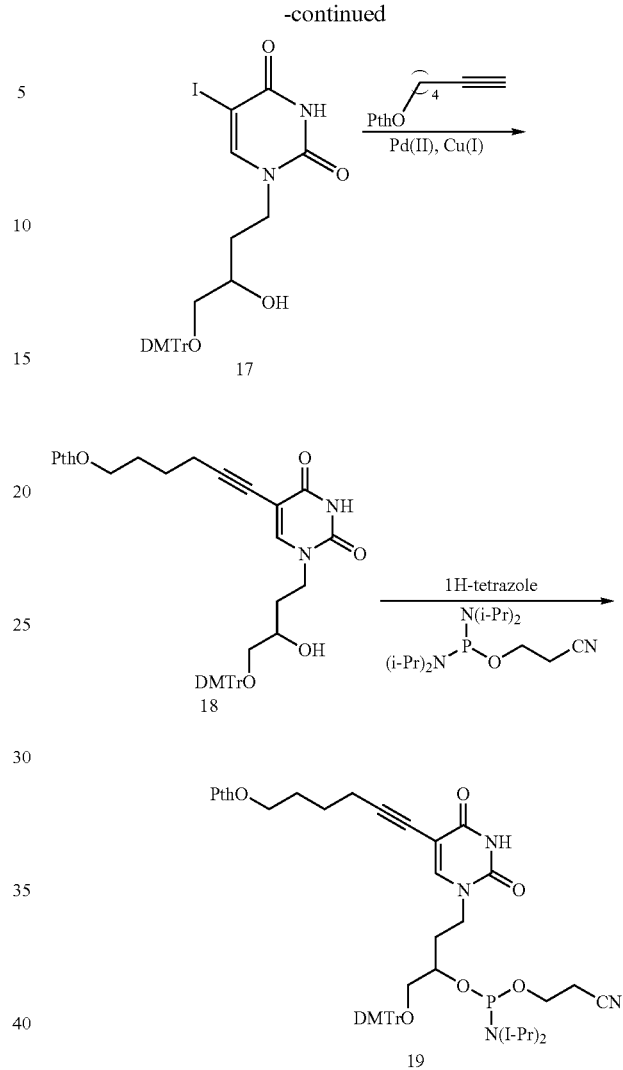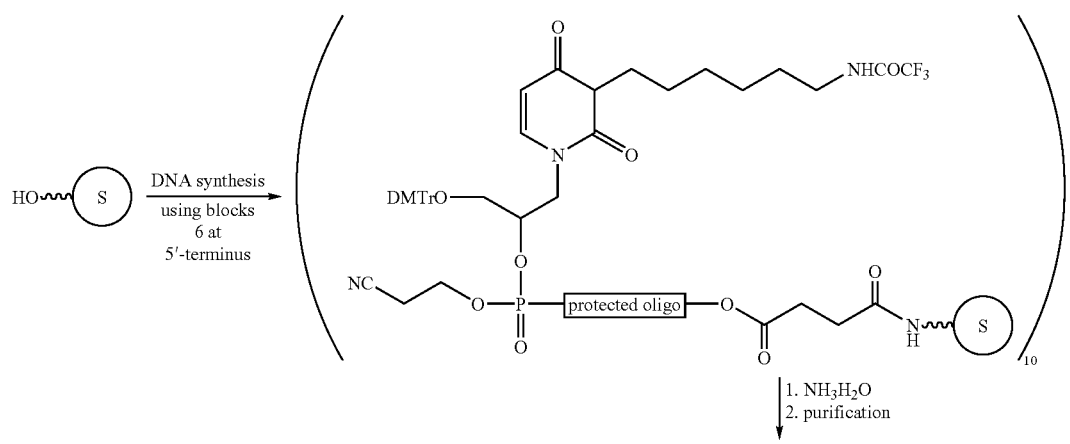

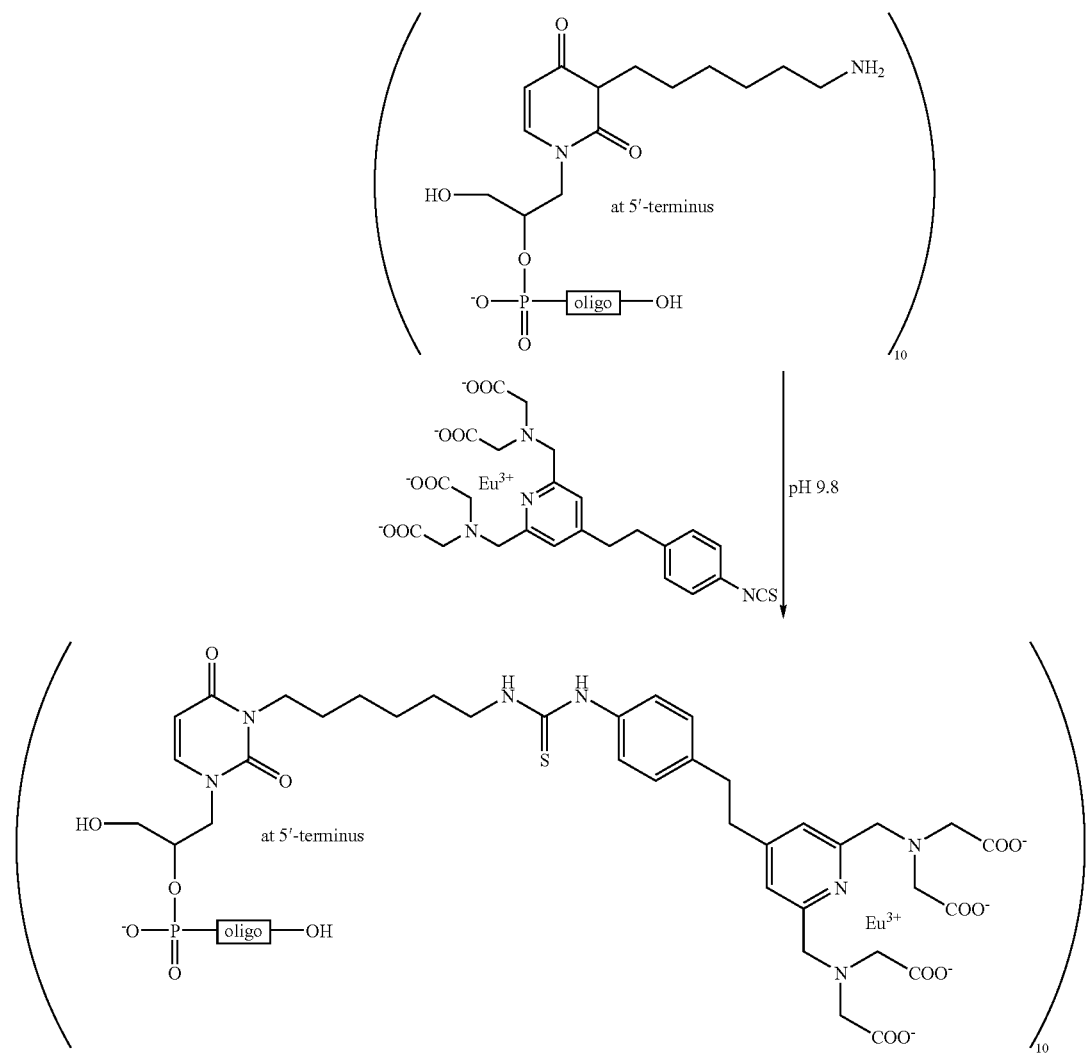
SCHEME 7
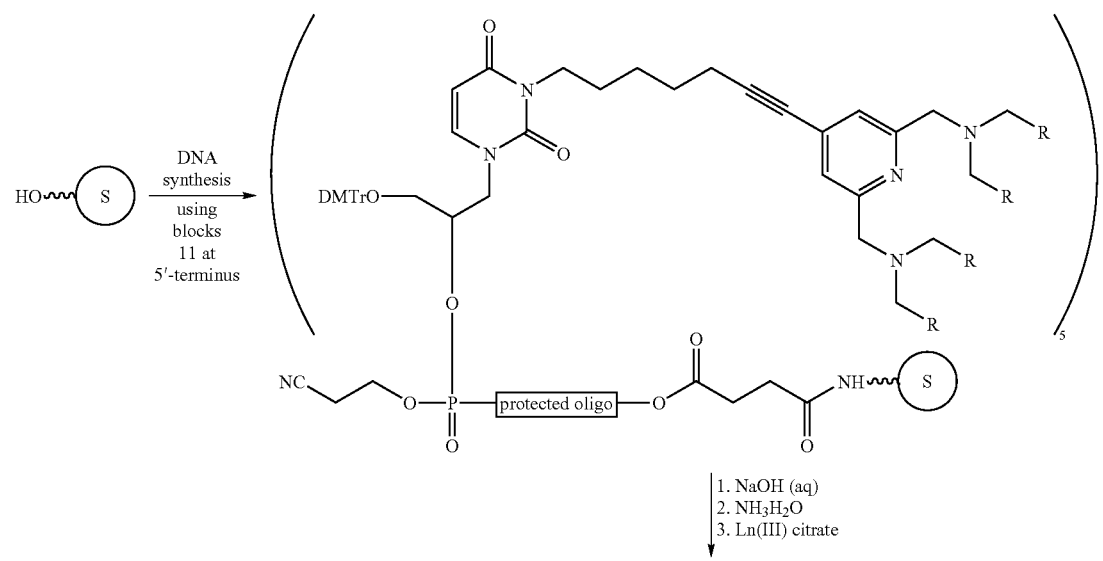

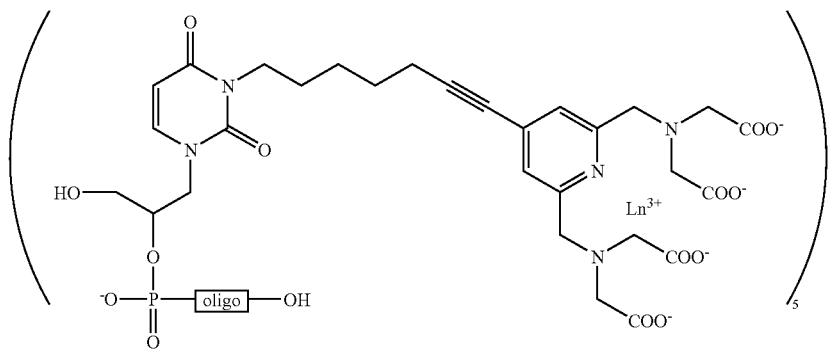
SCHEME 8
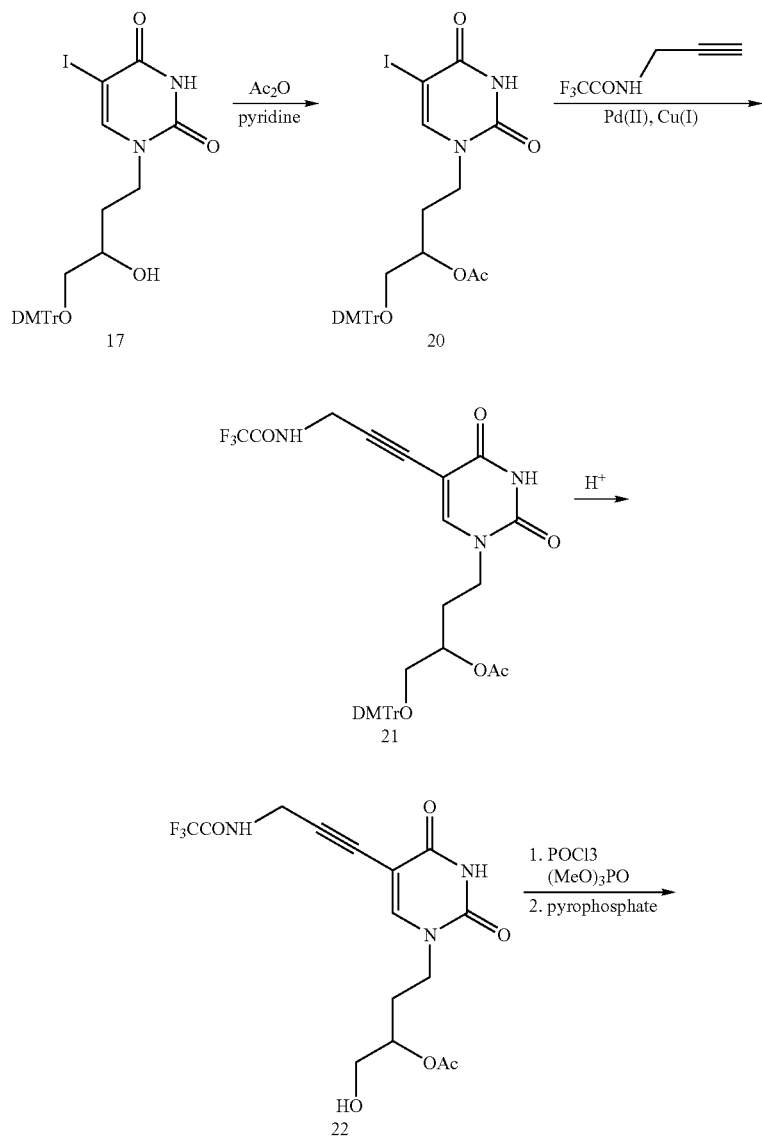

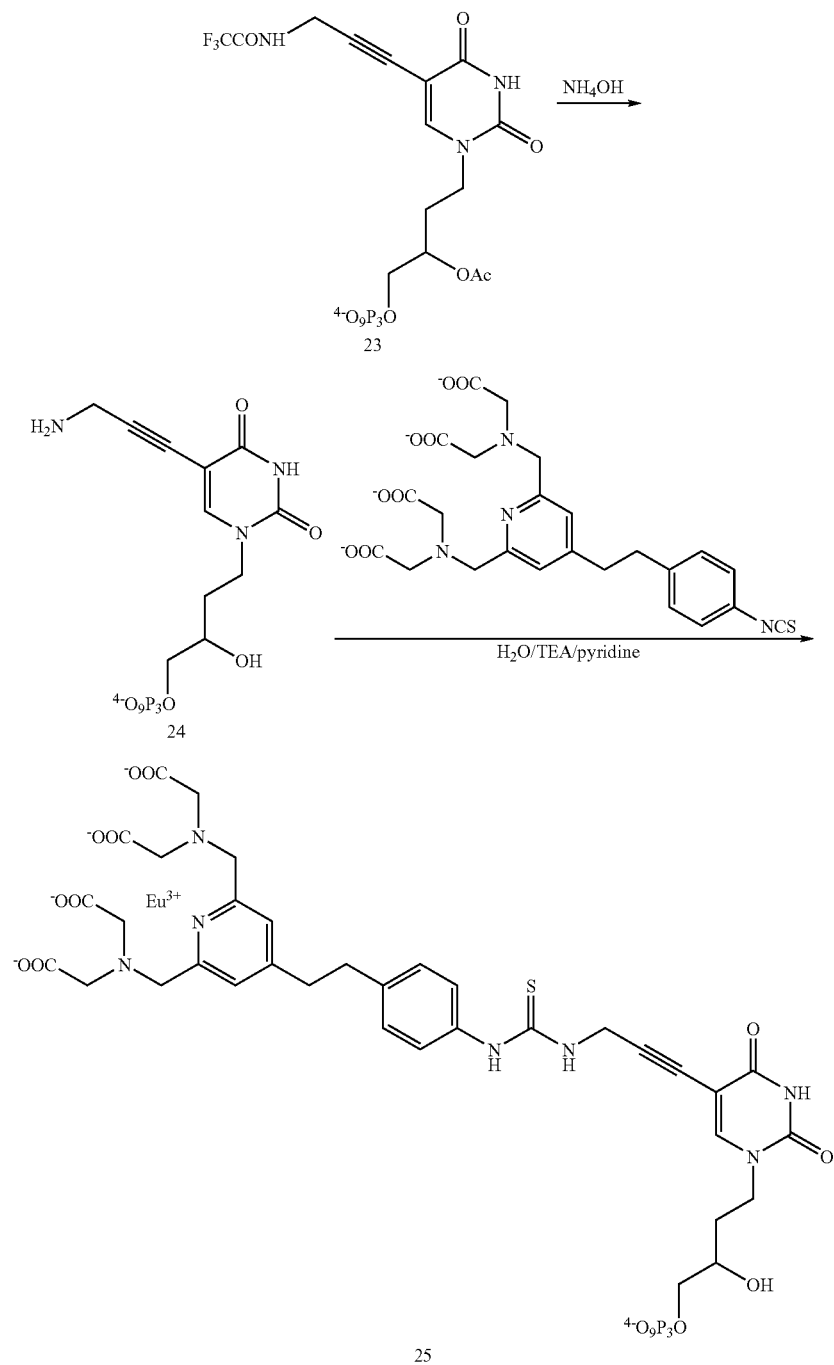

What is claimed is:

1. A labeling reactant of formula (I), useful for labeling an oligonucleotide using solid phase chemistry,

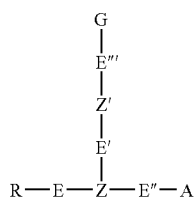

wherein
R is a protecting group or not present;
A is either a phosphorylating moiety

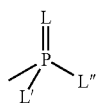

where
L is O, S, or not present
L' is H, $XCH_2CH_2CN$ or XAr, where Ar is phenyl or its substituted derivative, where the substituent is nitro or chlorine, and X is O or S;
L" is $O^-$, $S^-$, Cl, $N(i-Pr)_2$; or
A is a solid support tethered to Z via a linker arm E";
Z is a bridge point and is formed from

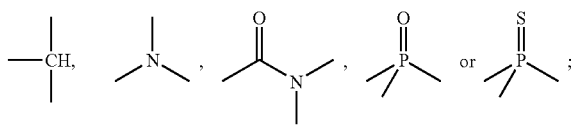

E is a linker arm between R and Z, E' is a linker arm between Z and Z', E" is a linker arm between Z and A and E''' is a linker arm between Z' and G, same or different, and is formed of one to ten moieties, each moiety being selected from the group consisting of phenylene, alkylene containing 1–12 carbon atoms, ethynediyl, ether, thioether, amide, carbonyl, ester, disulfide, diaza, and tertiary amine;
Z' is a pyrimidine base selected from the group consisting of cytosine, thymine, uracil, where E' is attached to N1 of pyrimidines, and E''' is attached to N3 or C5 of uracil, N3 of thymine, C5 or $N^4$ of cytosine, and where the exocyclic functional groups of said base are protected, or
Z' is selected from the group consisting of imidazole, pyrazolo[3,4-d]pyrimidine, 4-amino-pyrazolo[3,4-d]pyrimidine, 1,2,4-triazine-3,5-dione, 5-amino-1,2,4-triazine-3-one, where E' is attached to N1 of imidazole, N2 of 1,2,4-triazine-3,5-dione and 5-amino-1,2,4-triazine-3-one, and N7 of 4-amino-pyrazolo[3,4-d]pyrimidine and pyrazolo[3,4-d]pyrimidine, and E" is attached to C4 or C5 of imidazole, C2 or C9 of 4-amino-pyrazolo[3,4-d]pyrimidine, C2, C4 or C9 of pyrazolo[3,4-d]pyrimidine, N4, C5 or C6 of 1,2,4-triazine-3,5-dione and $N^5$ or C6 of $N^5$-amino 1,2,4-triazine-3,5-dione and where the exocyclic functional groups of said base are protected;
G is a protected bivalent aromatic structure, tethered to two iminodiacetic acid ester groups $N(CH_2COOR")_2$ where
R" is an alkyl of 1 to 4 carbon atoms, allyl, ethyltrimethylsilyl, phenyl or benzyl, which phenyl or benzyl is substituted or unsubstituted, and
one of the hydrogen atoms is substituted with E''', and
said bivalent aromatic structure is capable of absorbing light or energy and transferring the excitation energy to a lanthanide ion after said labeling reactant has been deprotected and converted to a lanthanide chelate, or
G is a structure selected from the group consisting of

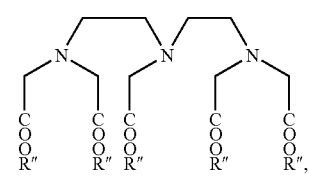

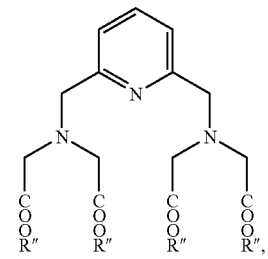

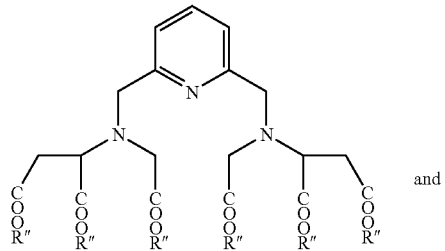

and

-continued

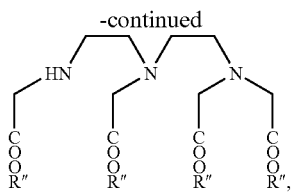

where
- R'' is an alkyl of 1 to 4 carbon atoms, allyl, ethyltrimethylsilyl, phenyl or benzyl, which phenyl or benzyl is substituted or unsubstituted, and one of the hydrogen atoms is substituted with E''', or
- G is a protected functional group, where the functional group is amino, aminooxy, carboxyl, thiol, and the protecting group is pthaloyl, trityl, 2-(4-nitrophenylsulfonyl)ethoxycarbonyl, fluorenylmethyloxycarbonyl, benzyloxycarbonyl, t-butoxycarbonyl or trifluoroacetuyl for amino and aminooxy, alkyl for carbonyl and alkyl or trityl for thiol, or
- G is a protected or unprotected organic dye, hapten or a spin label.

2. The labeling reactant according to claim 1 wherein G is a protected functional group.

3. The labeling reactant according to claim 1 wherein G is an organic dye.

4. The labeling reactant according to claim 1 wherein G is a hapten.

5. The labeling reactant according to claim 1 wherein the protecting group R is 4,4'dimethoxytrityl (DMTr).

6. The labeling reactant according to claim 1 wherein G is a bivalent aromatic structure.

7. The labeling reactant according to claim 1 wherein said labeling reactant is non-luminescent and G is selected from the group consisting of

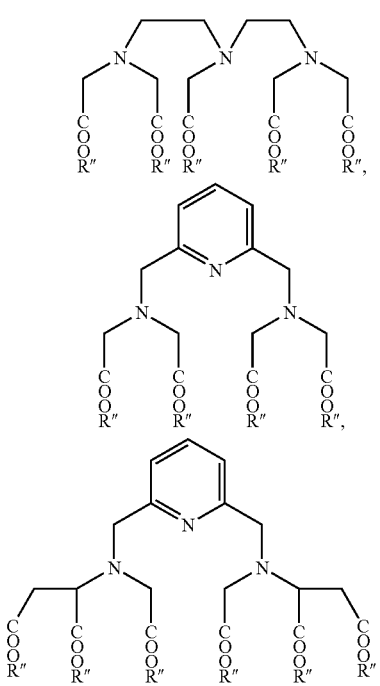

and

-continued

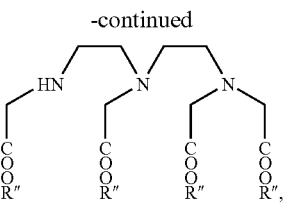

where
- R''' is an alkyl of 1 to 4 carbon atoms, allyl, ethyltrimethylsilyl, phenyl or benzyl, which phenyl or benzyl can be substituted or unsubstituted, and
- one of the hydrogen atoms is substituted with E'''.

8. The labeling reactant according to claim 7 wherein R'' is selected from the group consisting of methyl, ethyl and allyl.

9. The labeling reactant according to claim 1 wherein the labeling reactant is selected from the group consisting of
- (S)-1-[3-(4,4'-dimethoxytrityl-2,3-dihydroxypropyl)-3-O-(2-cyanoethyl N,N-diisopropyl)phosphoramidato)-3-(N6-trifluoroacetamidohexyl)uracil (6),
- (S)-1-[3-(4,4'-dimethoxytrityl-2,3-dihydroxypropyl-2-O-(2-cyanoethyl N,N-diisopropyl)phosphoramidato)]-1-{tetramethyl 2,2',2'',2'''-[(4-(hex-5-yn-1-yl)pyridine-2,6-diyl]bis(methylenenitrilo)}tetrakis(acetato)uracil (11),
- (S)-1-[3-(4,4'-dimethoxytrityl-2,3-dihydroxypropyl)-2-O-(2-cyanoethyl N,N-diisopropyl)phosphoramidato)]-1-[3-(2,2',2'',2'''-{[4'-(4''-(5-hexyn-6-yl)phenyl)-2,2':6',2''-terpyridine-6,6''-diyl]bis(methylenenitrilo)}tetrakis(acetato)uracil (13) and
- (S)-1-[(3,4-dihydroxybutyl-4-O-(4,4'-dimethoxytrityl)-3-O-(2-cyanoethyl N,N-diisopropyl)phosphoramidato]-1-(5-hydroxypthalimidohexynyluracil) (19).

10. A labeling reactant of formula (II), useful for labeling an oligonucleotide using polymerases, for labeling an oligonucleotide using solid phase chemistry, $$\begin{array}{c} G \\ | \\ E''' \\ | \\ Z' \\ | \\ E' \\ | \\ R''''{-}E{-}Z{-}E''{-}OH \end{array} \qquad (II)$$

wherein
R'''' is

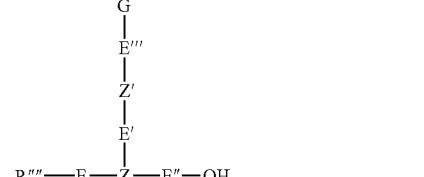

or salts thereof;

Z is a bridge point and is formed from

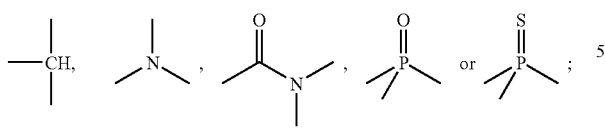

E is a linker arm between R'''' and Z, E' is a linker arm between Z and Z', E'' is a linker arm between Z and A and E''' is a linker arm between Z' and G', same or different, and is formed of one to ten moieties, each moiety being selected from the group consisting of phenylene, alkylene containing 1–12 carbon atoms, ethynediyl, ether, thioether, amide, carbonyl, ester, disulfide, diaza, amine and tertiary amine;

Z' is a pyrimidine base selected from the group consisting of cytosine, thymine, uracil, where E' is attached to N1 of pyrimidines, and E''' is attached to C5 of uracil, C5 or $N^4$ of cytosine, or Z' is selected from the group consisting of imidazole, pyrazolo[3,4-d]pyrimidine, 4-amino-pyrazolo[3,4-d]pyrimidine, 1,2,4-triazine-3,5-dione, 5-amino-1,2,4-triazine-3-one, where E' is attached to N1 of imidazole, N2 of 1,2,4-triazine-3,5-dione and 5-amino-1,2,4-triazine-3-one, and N7 of 4-amino-pyrazolo[3,4-d]pyrimidine and pyrazolo[3,4-d]pyrimidine, and E'' is attached to C4 or C5 of imidazole, C2 or C9 of 4-amino-pyrazolo[3,4-d]pyrimidine, C2, C4 or C9 of pyrazolo[3,4-d]pyrimidine, N4, C5 or C6 of 1,2,4-triazine-3,5-dione and $N^5$ or C6 of $N^5$-amino 1,2,4-triazine-3,5-dione;

G' is a bivalent aromatic structure, tethered to two iminodiacetic acid groups $N(CH_2COOH)_2$, or salts thereof, and is chelating a lantanide(III) ion where one of the hydrogen atoms is substituted with E''', and the lantanide(III)(Ln) ion is europium(Eu), samarium (Sm), terbium(Tb), or dysprosium(Dy) and said bivalent aromatic structure is capable of absorbing light or energy and transferring the excitation energy to a lanthanide ion, or G' is a structure selected from a group consisting of

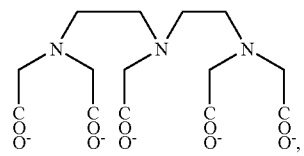

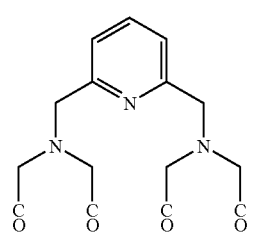

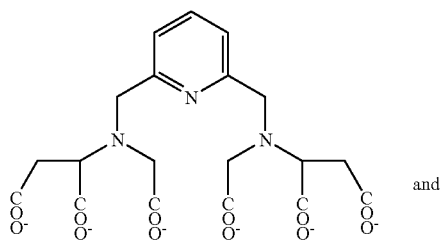

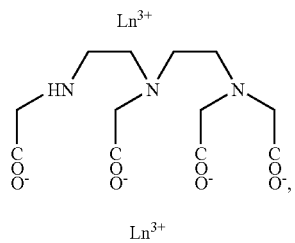

or salts thereof, where one of the hydrogen atoms is substituted with E''' and Ln is Nu, Tb, Sm or Dy, or G' is a functional group, or G' is an organic dye, hapten or a spin label.

11. The labeling reactant according to claim 10 wherein G' is a functional group.

12. The labeling reactant according to claim 10 wherein G' is an organic dye.

13. The labeling reactant according to claim 10 wherein G' is a hapten.

14. The labeling reactant according to claim 10 wherein G' is a bivalent aromatic structure.

15. The labeling reactant according to claim 10 wherein said labeling reactant is non-luminescent and G' is selected from the group consisting of

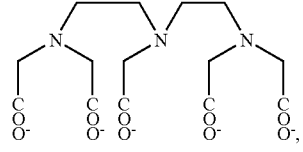

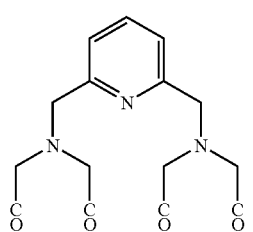

-continued

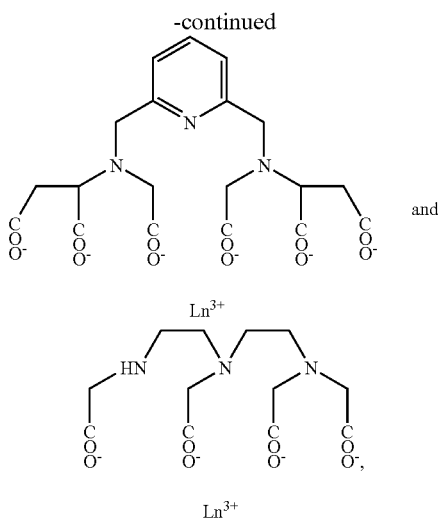

or salts thereof, where
one of the hydrogen atoms is substituted with E''' and Ln is Eu, Tb, Sm or Dy.

16. An oligonucleotide conjugate comprising a label wherein
a) it has been synthesized using a labeling reactant according to claim 1,
b) it comprises a coding sequence consisting of a natural DNA and/or RNA fragment or its monothioate, dithioate or phosphoramidate analogue, or a PNA oligonucleotide, or their mixture, and
c) said label, one or several, same or different, obtained, after
i) introduction of said labeling reactant,
ii) introduction and deprotection of said labeling reactant,
iii) introduction and deprotection of said labeling reactant followed by introduction of a lanthanide(III) ion when the label is a luminescent or non-luminescent lanthanide(III) chelate, or
iv) introduction and deprotection of said labeling reactant followed by introduction of a signaling moiety in solution as its thiocyanate, active ester, dichlorotriazine, aldehyde, ketone, or haloacetamido derivative when said labeling reactant comprises a deprotected functional group,
is attached to the 3'- or/and 5'-terminus of the oligonucleotide chain or/and within the coding sequence.

17. An oligonucleotide conjugate comprising a label wherein
a) it has been synthesized using a labeling reactant according to claim 10,
b) it comprises a coding sequence consisting of a natural DNA and/or RNA fragment or its monothioate, dithioate or phosphoramidate analogue, or a PNA oligonucleotide, or their mixture, and
c) said label, one or several, same or different, obtained, after
i) introduction of said labeling reactant,
ii) introduction and deprotection of said labeling reactant,
iii) introduction and deprotection of said labeling reactant followed by introduction of a lanthanide(III) ion when the label is a luminescent or non-luminescent lanthanide(III) chelate, or
iv) introduction and deprotection of said labeling reactant followed by introduction of a signaling moiety in solution as its thiocyanate, active ester, dichlorotriazine, aldehyde, ketone, or haloacetamido derivative when said labeling reactant comprises a deprotected functional group,
is attached to the 3'- or/and 5'-terminus of the oligonucleotide chain or/and within the coding sequence.

18. The labeling reactant of claim 1, wherein R is a member of the group consisting of 4,4'-dimethoxytrityl, 4-methoxytrityl, trityl, and (9-phenyl)xanthen-9-yl.

19. The labeling reactant of claim 1, wherein A is either controlled pore glass or polystyrene.

20. The labeling reactant of claim 1, wherein the exocyclic functional groups of Z' are selected from the group consisting of benzoyl, isobutyl and acetyl.

21. The labeling reactant of claim 2, wherein G is a protected functional group selected from the group consisting of amino, carboxyl, aminooxy and thiol.

22. The labeling reactant of claim 3, wherein G is an organic dye selected from the group consisting of dabsyl, dansyl, fluorescein, rhodamine and tetramethyl-6-carboxyrhodamine.

23. The labeling reactant of claim 4, wherein G is a hapten selected from the group consisting of biotin, dinitrophenol and digoxigenin.

24. The labeling reactant of claim 6, wherein G is a bivalent structure selected from the group consisting of carbostyryl,

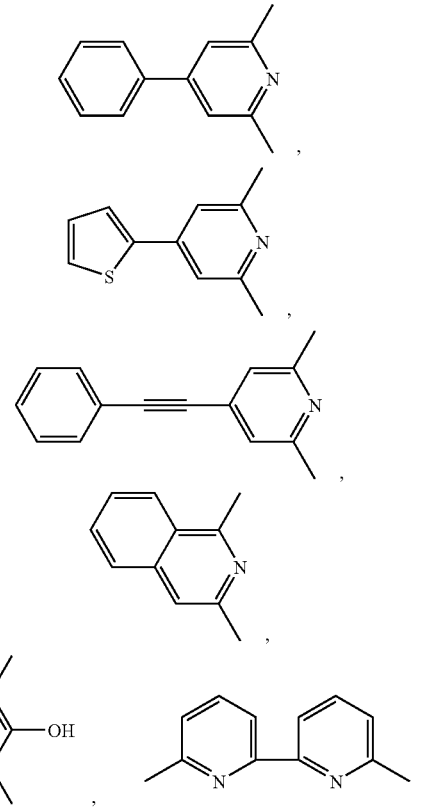

-continued

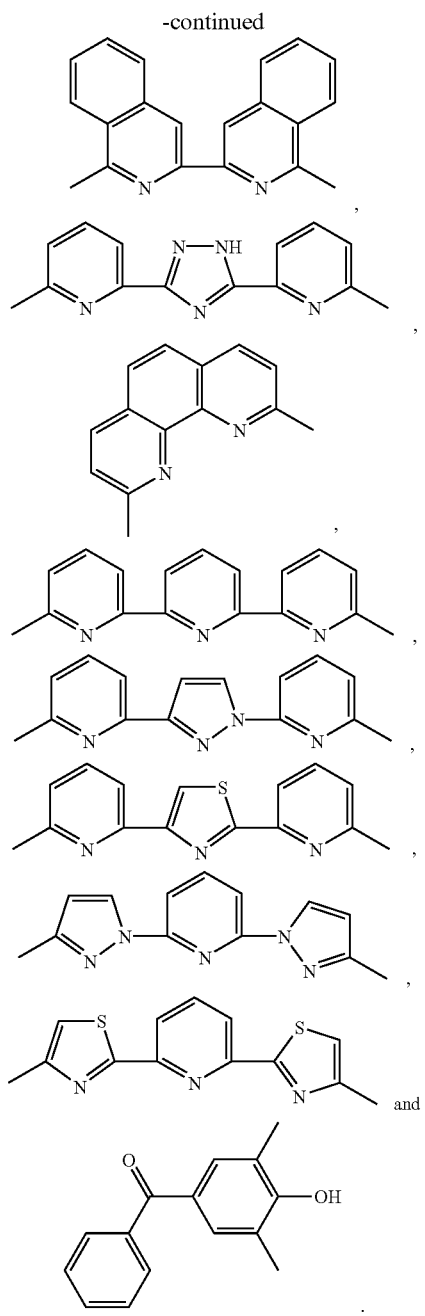

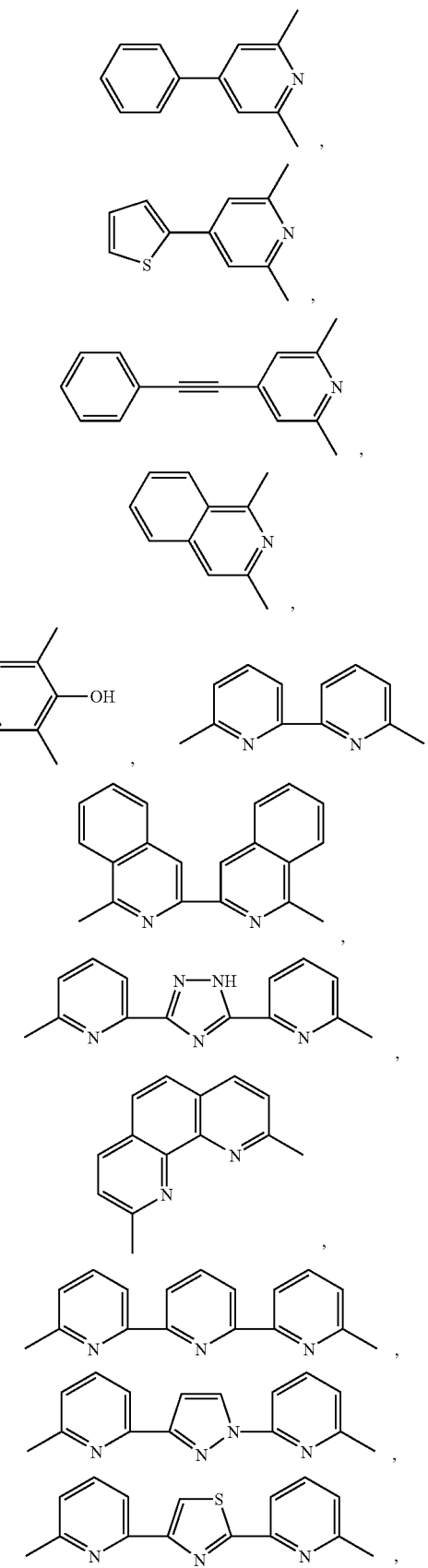

25. The labeling reactant of claim 11, wherein G' is a functional group selected from the group consisting of amino, carboxyl, aminooxy and thiol.

26. The labeling reactant of claim 12, wherein G' is an organic dye selected from the group consisting of dabsyl, dansyl, fluorescein, rhodamine and tetramethyl-6-carboxyrhodamine.

27. The labeling reactant of claim 13, wherein G' is a hapten selected from the group consisting of biotin, dinitrophenol and digoxigenin.

28. The labeling reactant of claim 14, wherein G' is a bivalent structure selected from the group consisting of carbostyryl, -continued
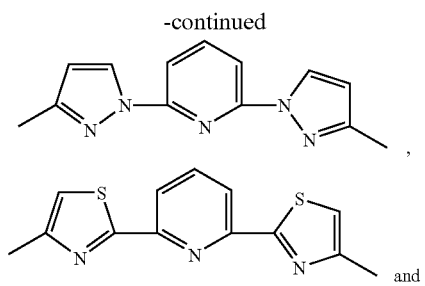
and
-continued
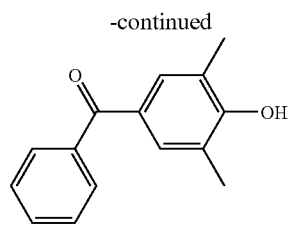
* * * * *

UNITED STATES PATENT AND TRADEMARK OFFICE
CERTIFICATE OF CORRECTION

| | | |
|---|---|---|
| PATENT NO. | : 7,282,581 B2 | Page 1 of 1 |
| APPLICATION NO. | : 09/985454 | |
| DATED | : October 16, 2007 | |
| INVENTOR(S) | : Jari Hovinen | |

It is certified that error appears in the above-identified patent and that said Letters Patent is hereby corrected as shown below:

IN THE SPECIFICATION:
Col. 29 & 30, please insert -- Eu3+ -- into the europium chelate of 4-[2-(4-isothiocyanatophenyl)ethyl]-2,6-bis[[N,N-bis(carboxymethyl)amino]methyl]pyridine:

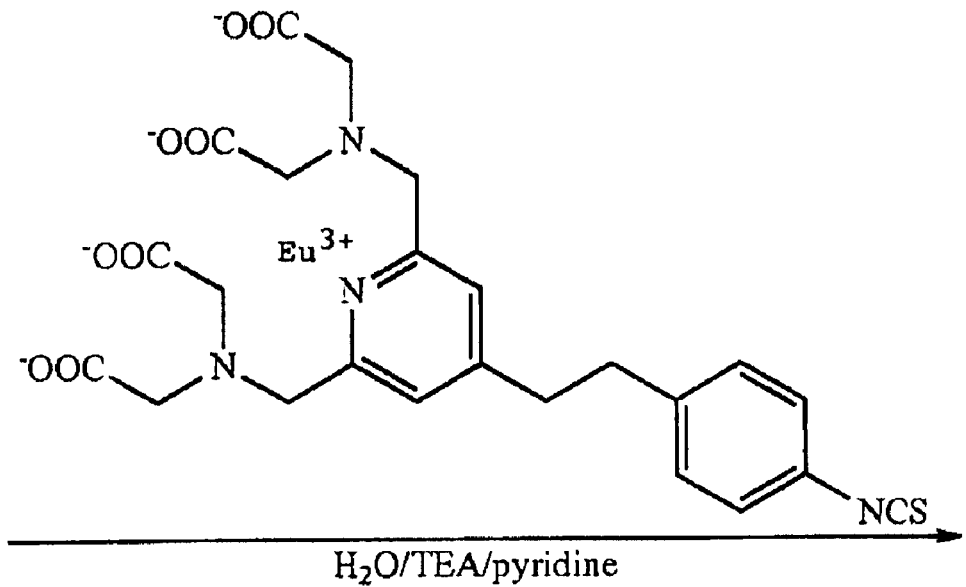

IN THE CLAIMS:
Claim 10, Col. 36, line 26, change "Nu" to -- Eu --.

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,282,581 B2 | Page 1 of 1 |
| APPLICATION NO. | : 09/985454 | |
| DATED | : October 16, 2007 | |
| INVENTOR(S) | : Hovinen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1243 days.

Signed and Sealed this

Ninth Day of November, 2010

David J. Kappos
*Director of the United States Patent and Trademark Office*